United States Patent
Li et al.

(10) Patent No.: US 11,890,168 B2
(45) Date of Patent: Feb. 6, 2024

(54) HEARING PROTECTION AND SITUATIONAL AWARENESS SYSTEM

(71) Applicant: Li Creative Technologies Inc., Florham Park, NJ (US)

(72) Inventors: Qi Li, New Providence, NJ (US); Yin Ding, Livingston, NJ (US)

(73) Assignee: LI CREATIVE TECHNOLOGIES INC.

( * ) Notice: Subject to any disclaimer, the term of this patent is extended or adjusted under 35 U.S.C. 154(b) by 0 days.

(21) Appl. No.: 18/186,972

(22) Filed: Mar. 21, 2023

(65) Prior Publication Data

US 2023/0329913 A1    Oct. 19, 2023

Related U.S. Application Data

(60) Provisional application No. 63/321,825, filed on Mar. 21, 2022.

(51) Int. Cl.
*H04R 5/027* (2006.01)
*G10L 15/22* (2006.01)
(Continued)

(52) U.S. Cl.
CPC ...... *A61F 11/145* (2022.01); *G10K 11/17823* (2018.01); *G10K 11/17881* (2018.01);
(Continued)

(58) Field of Classification Search
CPC ............ A61F 11/145; G10K 11/17823; G10K 11/17881; G10K 11/17825; G10K 2210/1081; G10K 2210/3026; G10K 2210/3027; G10K 2210/3028; G10K 2210/3044; G10K 2210/3046;
(Continued)

(56) References Cited

U.S. PATENT DOCUMENTS 5,303,308 A * 4/1994 Larsen ................ H04M 1/6016
                                            381/72
8,861,756 B2   10/2014 Zhu et al.
(Continued)

*Primary Examiner* — Carolyn R Edwards
*Assistant Examiner* — Friedrich Fahnert
(74) *Attorney, Agent, or Firm* — Ashok Tankha

(57) ABSTRACT

A hearing protection and situational awareness system includes a wearable device, speakers, one or more beamformers, a microphone array, and a computation unit. The system generates a three-dimensional (3D) binaural sound for enhanced situational awareness; provides hearing protection by active noise cancelation; provides hearing enhancement by automatic gain control; and performs background noise reduction and cancelation. The system performs automated sound detection, identification, and localization, with automated voice assistance, and facilitates clear two-way communications. Each beamformer(s) outputs a sound track associated with a sound captured by the microphone array in a direction(s) of an acoustic beam pattern(s). The computation unit combines filtered sound tracks generated using head-related transfer function (HRTF) filters into left and right sound channels to drive the speaker(s) in left and right hearing members of the wearable device, respectively, thereby generating a 3D binaural sound including cues of the sound source directions.

15 Claims, 20 Drawing Sheets

(51) Int. Cl.
*G10L 25/51* (2013.01)
*A61F 11/14* (2006.01)
*H04R 3/00* (2006.01)
*H04R 5/033* (2006.01)
*G10K 11/178* (2006.01)
*H04S 7/00* (2006.01)
*H04R 1/10* (2006.01)
*H04S 1/00* (2006.01)

(52) U.S. Cl.
CPC .............. *G10L 15/22* (2013.01); *G10L 25/51* (2013.01); *H04R 1/1008* (2013.01); *H04R 1/1083* (2013.01); *H04R 3/005* (2013.01); *H04R 5/027* (2013.01); *H04R 5/0335* (2013.01); *H04S 1/007* (2013.01); *H04S 7/304* (2013.01); *G10K 11/17825* (2018.01); *G10K 2210/1081* (2013.01); *G10K 2210/3026* (2013.01); *G10K 2210/3027* (2013.01); *G10K 2210/3028* (2013.01); *G10K 2210/3044* (2013.01); *G10K 2210/3046* (2013.01); *H04R 2201/107* (2013.01); *H04R 2460/01* (2013.01); *H04S 2400/11* (2013.01); *H04S 2400/13* (2013.01); *H04S 2400/15* (2013.01); *H04S 2420/01* (2013.01)

(58) Field of Classification Search
CPC ....... G10L 15/22; G10L 25/51; H04R 1/1008; H04R 1/1083; H04R 3/005; H04R 5/027; H04R 5/0335; H04R 2201/107; H04R 2460/01; H04S 1/007; H04S 7/304; H04S 2400/11; H04S 2400/13; H04S 2400/15; H04S 2420/01
USPC .......................................................... 381/309
See application file for complete search history.

(56) References Cited

U.S. PATENT DOCUMENTS

| | | | |
|---|---|---|---|
| 9,131,305 B2 | 9/2015 | Li et al. | |
| 9,418,675 B2 | 8/2016 | Zhu et al. | |
| RE47,049 E | 9/2018 | Zhu et al. | |
| RE48,371 E | 12/2020 | Zhu et al. | |
| 11,240,621 B2 | 2/2022 | Li et al. | |
| 2012/0215519 A1* | 8/2012 | Park | H04R 3/005 381/17 |
| 2013/0094657 A1* | 4/2013 | Brammer | G10K 11/17881 381/71.6 |
| 2014/0198918 A1* | 7/2014 | Li | H04S 7/30 381/26 |
| 2017/0374455 A1* | 12/2017 | Shastry | H04R 1/1008 |
| 2018/0338201 A1* | 11/2018 | Mann | H04R 1/1083 |
| 2019/0387304 A1* | 12/2019 | Song | G06F 3/165 |
| 2020/0058285 A1* | 2/2020 | Parikh | G10K 11/17881 |
| 2020/0128322 A1* | 4/2020 | Sabin | G06F 3/012 |
| 2020/0196058 A1* | 6/2020 | Udesen | H04S 7/304 |
| 2021/0211814 A1* | 7/2021 | Tripathi | G10L 25/51 |
| 2021/0321212 A1 | 10/2021 | Li et al. | |
| 2023/0010505 A1* | 1/2023 | Ganeshkumar | G10L 25/81 |

* cited by examiner

| Sound ID  | Airplane | Gunshot | Helicopter | Tank | Truck | Footsteps |
|-----------|----------|---------|------------|------|-------|-----------|
| Airplane  | 52       | 0       | 0          | 0    | 0     | 0         |
| Gunshot   | 0        | 53      | 0          | 0    | 0     | 0         |
| Helicopter| 1        | 0       | 50         | 0    | 0     | 0         |
| Tank      | 0        | 0       | 1          | 49   | 0     | 0         |
| Truck     | 0        | 0       | 1          | 0    | 61    | 0         |
| Footsteps | 0        | 0       | 0          | 0    | 0     | 50        |

FIG. 7B

HEARING PROTECTION AND SITUATIONAL AWARENESS SYSTEM

CROSS-REFERENCE TO RELATED APPLICATIONS

This application claims priority to and the benefit of the provisional patent application titled "Hearing Protection and Situational Awareness System", application No. 63/321,825, filed in the United States Patent and Trademark Office on Mar. 21, 2022. The specification of the above referenced patent application is incorporated herein by reference in its entirety.

BACKGROUND

Situational awareness refers to an ability to know, perceive, and understand one's location, surroundings, and various occurrences in their surroundings and environment, allowing individuals to be more alert and make informed judgements, decisions, and reactions. Situational awareness allows individuals to be aware of pertinent factors, for example, potential hazards, opportunities, and changing circumstances, in their environment, and have a clear understanding of their significance and potential impact. Situational awareness is useful in various fields comprising, for example, industrial operations, ground operations, maritime operations, tactical operations, emergency response operations, firefighter operations, rescue operations, training, aviation, naval operations, gaming, etc., as well as in everyday life situations where being aware of one's surroundings can help prevent accidents and facilitate better decision-making. In operation and training scenarios, for example, there is a need for improving situational awareness by improving communications, improving auditory detection and localization in headgear and in-ear communications in high noise and low noise environments, and improving auditory preservation. Therefore, there is a need for applying a combination of advanced digital signal processing and artificial intelligence (AI) technologies comprising sound localization, sound identification, voice assistance, noise monitoring, noise cancelation, noise reduction, gain control, two-way communications, etc., to a system or a device implemented, for example, in wearable devices such as headsets, headphones, earphones, earbuds, etc., hereinafter referred to as "headphones", with suitable actuators.

Sound is typically heard in a mono or stereo audio format. Stereo is a method of reproducing sound that may use multiple independent audio channels played using two or more speakers or headphones so that the sound from the speakers or the headphones appears to be coming from various directions, thereby simulating natural hearing. However, stereo sound typically refers to merely two audio channels to be played using two speakers or headphones. Stereo sound is, therefore, different from "real" sound, for example, sound heard by a listener present in a tactical training scenario, because spatial information regarding individual sound sources, for example, vehicles, vocals, voices, gunshots, environmental noise, etc., is not reflected in the stereo sound. With two ears, a listener may perceive spatial information and hear real, three-dimensional (3D) sound, that is, the sound that comprises cues of sound source directions or locations. The 3D sound is then presented as binaural sound, that is, sound represented by a left ear sound channel and a right ear sound channel, thereby allowing the listener to hear the sound through the headphones as if the sound is perceived by two ears in a "real" acoustic environment such as a music hall, a theater, a sports stadium, or an arena. As used herein, "3D binaural sound" or "3D binaural audio" refers to sound or audio sent to left and right ears, respectively, containing the cues of the sound source directions or locations. The 3D binaural sound can be transmitted through conventional stereo channels, but conventional stereo does not contain cues of sound source directions or locations. As conventional sound technology typically provides only mono or stereo sound without spatial cues or spatial information, sounds may be experienced differently and often less optimally and informatively through conventional headphones.

In tactical, training, or gaming operations, headsets are required to have the ability to network with wireless communications systems and therefore, must provide sound quality to allow users to communicate easily and clearly. When a user wears a headset, the user's ears are blocked and the user cannot hear ambient sound well. Therefore, there is a need for a system that provides ambient sound along with cues of sound source directions to the user through left and right speakers. Unfortunately, as conventional headsets can provide only mono or stereo sound with minimal sound source direction information, vital sound direction information is lost because these headsets cannot provide 3D binaural sound and voice assistance. This drawback significantly reduces situational awareness and may compromise safety of individuals in operation and training scenarios.

Furthermore, with conventional tactical headsets that typically use only two microphones, one on each ear cup of the headset, it is difficult and in some instances impossible to achieve full 360-degree situational awareness because a sound wave from a right front direction and a right back direction can both arrive at the two microphones on the ear cups of the headset with no difference or with the same difference, thereby disallowing the headset user from distinguishing the sound waves. Therefore, there is a need for using an increased number of microphones in an array on a headset to identify sound source directions. Furthermore, conventional headsets receive uninformative auditory signals such as ambient noise equally as useful sound events, thereby making it difficult to amplify soft sound and attenuate ambient noise. When testing conventional headsets in a relatively quiet environment, the uninformative ambient noise was found to be significantly amplified. In this condition, the noise that is captured in a conventional headset is much louder than what is heard through bare ear listening, and almost dominates auditory awareness. Furthermore, the sound playback of some conventional headsets was found to be based on a dynamic range controller (DRC), which merely amplifies sound when the volume is low and attenuates the sound when the volume is high. However, much more frequently, the ambient noise was found to have a lower volume than the informative auditory signals. The procedure of amplifying ambient noise of low volume substantially degrades the signal-to-noise ratio (SNR) and compromises the user's hearing intelligibility.

Hence, there is a long-felt need for a system implemented in a wearable device, for example, a headset, with an array of multiple microphones, one or more beamformers, and a computation unit, configured to perform automated sound localization, identification, and control; generate acoustic beam patterns pointing to different sound source directions to enhance sounds from corresponding sound source directions and improve the signal-to-noise ratio (SNR) and hearing intelligibility; generate three-dimensional binaural sound with spatial cues or spatial information of individual sound source directions; provide voice assistance; and perform intelligent noise monitoring, reduction, and cancelation, for improving communications, improving auditory detection and localization in headgear and audio communications in high noise and low noise environments, and improving auditory preservation, and in turn, improving the performance and personal safety of a user in operations through both hearing protection and improved situational awareness, while also reducing training time.

SUMMARY OF THE INVENTION

This summary is provided to introduce a selection of concepts in a simplified form that are further disclosed in the detailed description of the invention. This summary is not intended to determine the scope of the claimed subject matter.

The system disclosed herein addresses the above-recited need for a system implemented in a wearable device, for example, a headset, with an array of multiple microphones, one or more beamformers, and a computation unit, configured to perform automated sound localization, identification, and control; generate acoustic beam patterns pointing to different sound source directions to enhance sounds from corresponding sound source directions and improve the signal-to-noise ratio (SNR) and hearing intelligibility; generate three-dimensional (3D) binaural sound with spatial cues or spatial information of individual sound source directions; provide voice assistance; and perform intelligent noise monitoring, reduction, and cancelation, for improving communications, improving auditory detection and localization in headgear and audio communications in high noise and low noise environments, and improving auditory preservation, and in turn, improving the performance and personal safety of a user in operations through both hearing protection and improved situational awareness, while also reducing training time. The system disclosed herein applies a combination of advanced digital signal processing (DSP) and artificial intelligence (AI) technologies comprising sound localization, sound identification, voice assistance, noise monitoring, noise cancelation, two-way noise reduction, far-field sound capture, gain control, two-way communications, etc., to the wearable device with suitable actuators comprising microphones and speakers. In an embodiment, the system implements an AI-based and DSP approach for the wearable device comprising a microphone array, advanced DSP algorithms, real-time software, voice assistance, and hardware. The system disclosed herein improves communication, localization, 3D situational awareness, and auditory preservation by leveraging the advanced DSP and AI technologies.

The system disclosed herein provides hearing protection and situational awareness. The system comprises a wearable device, for example, a headset, comprising hearing members, for example, ear cups. The hearing members comprise a left hearing member and a right hearing member. The left hearing member is configured to be disposed on a left ear of a user. The right hearing member is configured to be disposed on a right ear of the user. In an embodiment, the wearable device comprises a headband that connects the hearing members. In this embodiment, the hearing members are disposed on and attached to opposing ends of the headband. The headband is configured to be disposed on the user's head, and the hearing members are disposed on the user's ears. The system further comprises one or more speakers, a sound source localization unit, and a computation unit. The speaker(s) is disposed at an inner location of each of the hearing members of the wearable device. The sound source localization unit is operably coupled to the hearing members of the wearable device. The sound source localization unit comprises one or more beamformers and an array of outer microphones herein referred to as a "microphone array". Each beamformer is configured to generate one or more acoustic beam patterns pointing to one or more sound source directions. The array of outer microphones is disposed at outer locations of the hearing members of the wearable device. The array of outer microphones is configured to capture sound from at least one of the sound source directions of the acoustic beam patterns, outside of the hearing members. Each beamformer is configured to output a sound track. Each sound track is associated with the captured sound in a particular sound source direction(s) of the acoustic beam pattern(s).

The computation unit is disposed in one or more of the hearing members of the wearable device. The computation unit is operably coupled to the array of outer microphones of the wearable device. The computation unit comprises at least one processor and a memory unit operably and communicatively coupled to the processor(s). The memory unit is configured to store a database of head-related transfer function (HRTF) filters, and computer program instructions defined by multiple signal processing modules and executable by the processor(s). The signal processing modules comprise at least one 3D sound generator. For each beamformer, the 3D sound generator retrieves a pair of HRTF filters associated with the sound source direction(s) of the acoustic beam pattern(s) generated by each beamformer, from the database. The 3D sound generator applies the retrieved pair of HRTF filters to the output sound track from each beamformer, to generate two filtered sound tracks for the left ear and the right ear, respectively. Each of the two filtered sound tracks represents the sound captured from the particular sound source direction(s) of the acoustic beam pattern(s) and comprises a cue of the particular sound source direction(s). The 3D sound generator combines the filtered sound tracks generated for the left ear into a left sound channel to drive the speaker(s) in the left hearing member of the wearable device, and combines the filtered sound tracks generated for the right ear into a right sound channel to drive the speaker(s) in the right hearing member of the wearable device, thereby generating a 3D binaural sound comprising cues of the sound source directions. The speaker(s) in each of the hearing members of the wearable device reproduces real sound outside of the wearable device.

In an embodiment, the signal processing modules further comprise an AI-enabled sound identification module configured to automatically recognize characteristics of the captured sound and identify categories of the captured sound using one or more pretrained AI models. In an embodiment, the signal processing modules further comprise a voice assistant operably coupled to the speaker(s). The voice assistant, in communication with the AI-enabled sound identification module and the sound source localization unit, is configured to determine one or more sound source locations from the output sound track of each beamformer and to report the identified categories of the captured sound and a direction of the captured sound with voice assistance via the speaker(s) and/or one or more other interface devices.

In an embodiment, the signal processing modules further comprise one or more active noise cancelation (ANC) units configured to cancel noise captured by one or more inner microphones and to cancel background noise captured by the array of outer microphones, for improving hearing protection. The inner microphone(s) is disposed at an inner location of each of the hearing members of the wearable device. The inner microphone(s), operably coupled to the computation unit, is configured to facilitate active noise cancelation using the ANC unit(s). In an embodiment, the inner microphone(s) is configured as a noise dosimeter to monitor and record sound levels within the hearing members of the wearable device, and to communicate the recorded sound levels to a storage unit, for example, a secure digital (SD) card, for noise level analysis and review activities. In another embodiment, the computation unit further comprises one or more supplementary ANC units operably coupled to the array of outer microphones and the beamformer(s). For the output sound track of each beamformer, the supplementary ANC unit(s) is configured to cancel noise that is obtained from sound in other one or more output sound tracks of the other beamformers, from the output sound track, thereby enhancing the sound from the particular sound source direction(s) of the acoustic beam pattern(s) and reducing the noise from other sound source directions to improve the signal-to-noise ratio. In another embodiment, the signal processing modules further comprise an automatic gain control unit configured to control a level of output sound of the speaker(s) by selectively increasing gain when a level of the output sound is substantially low for hearing enhancement and situational awareness, and reducing the gain when the level of the output sound is substantially high for hearing protection.

In an embodiment, the system further comprises a supplementary microphone operably coupled to an adjustable arm extending from one of the hearing members of the wearable device. The supplementary microphone is configured to allow a user to speak thereinto for facilitating two-way communications. In an embodiment, the signal processing modules further comprise one or more noise reduction units configured to reduce noise in incoming audio signals and outgoing audio signals for improving the signal-to-noise ratio in two-way communications. In various embodiments, in addition to the 3D sound generator, the computation unit of the system comprises one or more of the other signal processing modules disclosed above in different combinations. For example, in an embodiment, the computation unit comprises the 3D sound generator and other signal processing modules, namely, the active noise cancelation (ANC) unit(s), the noise reduction unit(s), and the automatic gain control unit. In another embodiment, the computation unit comprises the 3D sound generator and other signal processing modules, namely, the AI-enabled sound identification module and the voice assistant. In another embodiment, the computation unit comprises the 3D sound generator and other signal processing modules, namely, the AI-enabled sound identification module, the voice assistant, the ANC unit(s), the noise reduction unit(s), and the automatic gain control unit.

In one or more embodiments, related systems comprise circuitry and/or programming for executing the methods disclosed herein. The circuitry and/or programming comprise one or any combination of hardware, software, and/or firmware configured to execute the methods disclosed herein depending upon the design choices of a system designer. In an embodiment, various structural elements are employed depending on the design choices of the system designer.

BRIEF DESCRIPTION OF THE DRAWINGS

The foregoing summary, as well as the following detailed description of the invention, is better understood when read in conjunction with the appended drawings. For illustrating the embodiments herein, exemplary constructions of the embodiments are shown in the drawings. However, the embodiments herein are not limited to the specific components, structures, and methods disclosed herein. The description of a component, or a structure, or a method step referenced by a numeral in a drawing is applicable to the description of that component, or structure, or method step shown by that same numeral in any subsequent drawing herein.

FIG. 7B illustrates an exemplary confusion matrix of sound identification.

DETAILED DESCRIPTION OF THE INVENTION

Figure 1A:
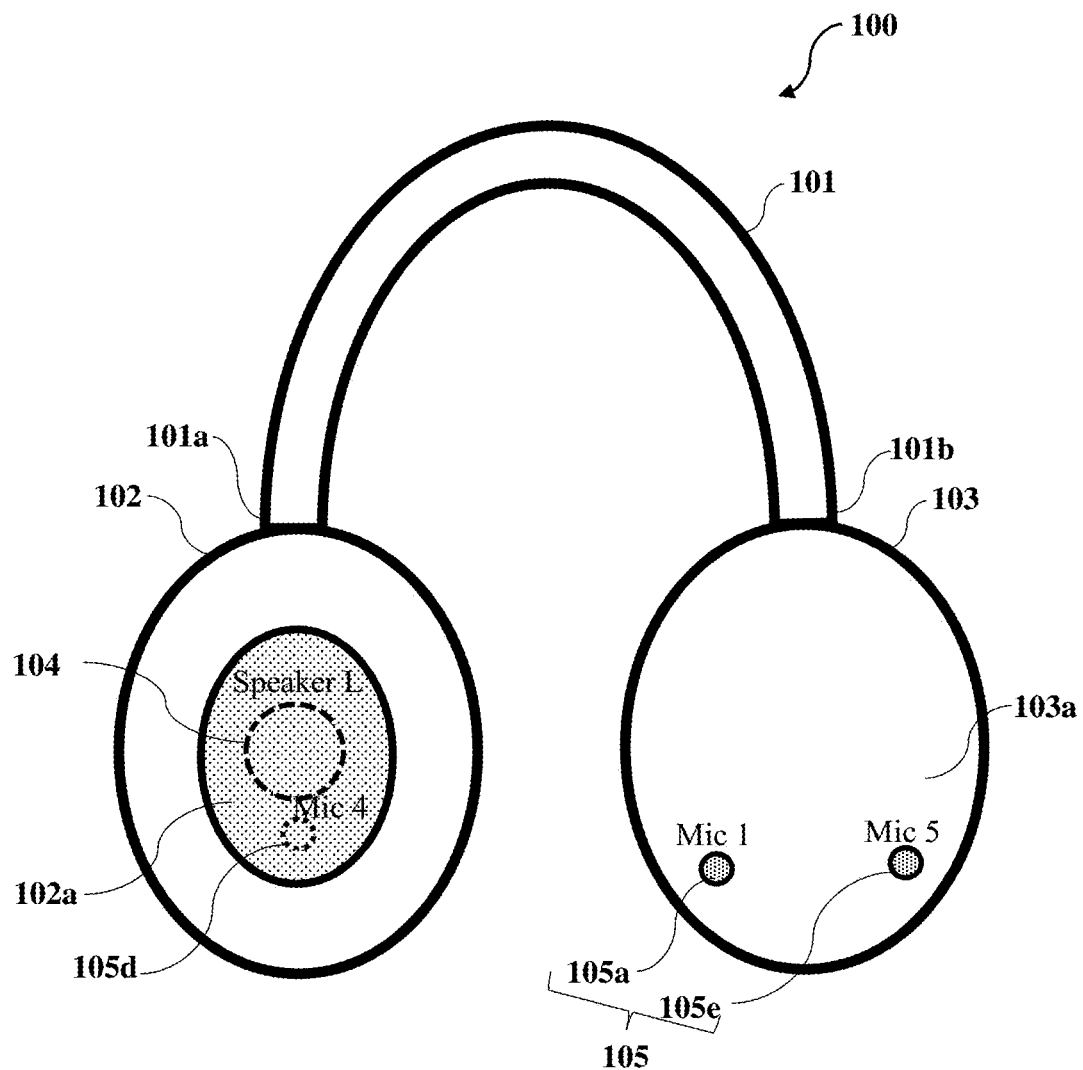
FIGS. 1A-1B illustrate perspective views of an embodiment of a wearable device comprising ear cups, speakers, an array of outer microphones, and inner microphones, for providing hearing protection and situational awareness.
Figure 1B:
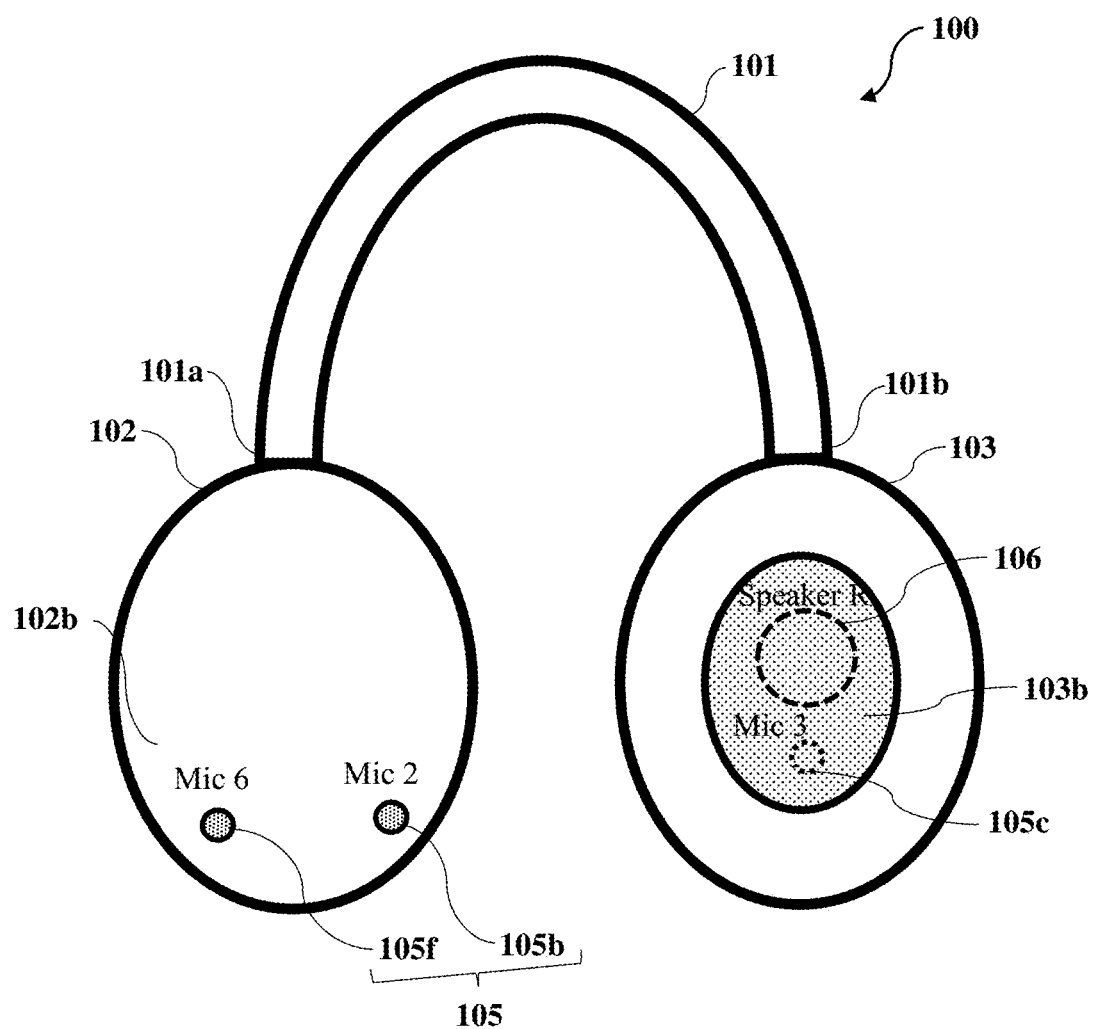

Various aspects of the disclosure herein are embodied as a system, a method, or a non-transitory, computer-readable storage medium having one or more computer-readable program codes stored thereon. Accordingly, various embodiments of the disclosure herein take the form of an entirely hardware embodiment, an entirely software embodiment comprising, for example, microcode, firmware, software, etc., or an embodiment combining software and hardware aspects that are referred to herein as a "system", a "module", a "circuit", or a "unit". Disclosed herein is an embodiment of a system comprising a wearable device 100 with a pair of speakers 104 and 106, an array of outer microphones 105$a$, 105$e$, 105$b$, and 105$f$, herein referred to as a microphone array 105, and inner microphones 105$c$ and 105$d$ as illustrated in FIGS. 1A-1B, for providing hearing protection and situational awareness. The system disclosed herein implements technologies that improve communications, localization, auditory preservation, and three-dimensional (3D) situational awareness for operation and training scenarios. The system implements digital signal processing (DSP) and actuators, for example, speakers and microphones, and applies the aforementioned technologies into a wearable device 100, for example, a headset.

FIGS. 1A-1B illustrate perspective views of an embodiment of a wearable device 100 comprising ear cups 102 and 103, speakers 104 and 106, an array 105 of outer microphones 105$a$, 105$b$, 105$e$, and 105$f$, herein referred to as a "microphone array" 105, and inner microphones 105$c$ and 105$d$, for providing hearing protection and situational awareness. In an embodiment as illustrated in FIGS. 1A-1B, the wearable device 100 is configured as a headset comprising a headband 101 and a pair of ear cups 102 and 103. The headband 101 is configured to be worn on a user's head. As used herein, the term "user" refers to an individual who wears or uses the wearable device 100 for hearing sound, for example, for face-to-face communication, radio communication, training activities, operations, etc. The headband 101 holds the ear cups 102 and 103 over the user's ears. The ear cups 102 and 103 are hearing members disposed on and attached to opposing ends 101$a$ and 101$b$ of the headband 101, respectively. A user may use one or both of the ear cups 102 and 103. The user may also use one of the ear cups 102 and 103 without the headband 101. The left ear cup 102 is configured to be disposed on the user's left ear. The right ear cup 103 is configured to be disposed on the user's right ear. For purposes of illustration, the disclosure herein refers to a headset comprising a headband 101 and a pair of ear cups 102 and 103 as the wearable device 100; however, the scope of the disclosure herein is not limited to the wearable device 100 being a headset comprising a headband 101 and a pair of ear cups 102 and 103, but extends to include any wearable device such as headphones, earphones, earbuds, etc., used in telephony and radio communication for hearing sound. Furthermore, in an embodiment, the wearable device 100 comprises one or more speakers and one or more inner microphones disposed in each of the ear cups 102 and 103.

As illustrated in FIGS. 1A-1B, a pair of speakers, for example, a left speaker 104 and a right speaker 106, of the wearable device 100 is disposed at inner locations, for example, inner surfaces 102$a$ and 103$b$ of the ear cups 102 and 103, respectively, and covered by an acoustically transparent material. The pair of speakers 104 and 106 is configured to facilitate generation of three-dimensional (3D) binaural sound. As used herein, "3D sound" refers to sound with cues of sound source directions or locations, and "binaural sound" refers to 3D sound represented by left ear and right ear sound channels with spatial information. 3D binaural sound, therefore, refers to sound containing the cues of the sound source directions or locations, sent to the left and right ears. From the 3D binaural sound, a listener can hear the cues of outside sound source directions/locations by wearing the left and right ear cups 102 and 103, respectively. The system disclosed herein identifies sound source directions, herein also referred to as sound source locations. Furthermore, the microphone array 105 comprises outer microphones 105$b$, 105$f$, and 105$a$, 105$e$ disposed at outer locations of the ear cups 102 and 103 of the wearable device 100, respectively. The inner microphones 105$c$ and 105$d$ are disposed at inner locations of the ear cups 103 and 102 of the wearable device 100, respectively.

In an exemplary implementation illustrated in FIGS. 1A-1B, the wearable device 100 comprises a 4-microphone array 105 mounted on outer surfaces 102$b$ and 103$a$ of the ear cups 102 and 103, respectively, which are covered by soft materials, and two microphones 105$d$ and 105$c$ mounted on inner surfaces 102$a$ and 103$b$ of the ear cups 102 and 103, respectively, which are covered by an acoustically transparent material. For example, one inner microphone 105$d$ is disposed on an inner surface 102$a$ of the left ear cup 102 as illustrated in FIG. 1A, and another inner microphone 105$c$ is disposed on an inner surface 103$b$ of the right ear cup 103 as illustrated in FIG. 1B. The inner microphones 105$c$ and 105$d$ are configured to facilitate active noise cancelation as disclosed in the description of FIG. 11. In an embodiment, the inner microphones 105$c$ and 105$d$ are configured as a noise dosimeter to monitor and record sound levels within the ear cups 103 and 102 of the wearable device 100, respectively, and to communicate the recorded sound levels to a storage unit, for example, a secure digital (SD) card (not shown), for noise level analysis and review activities. Furthermore, in an example, two outer microphones 105$a$ and 105$e$ are disposed on an outer surface 103$a$ of the right ear cup 103 as illustrated in FIG. 1A, and another two outer microphones 105$b$ and 105$f$ are disposed on an outer surface 102$b$ of the left ear cup 102 as illustrated in FIG. 1B. The outer microphones 105$a$, 105$e$, 105$b$, and 105$f$ are configured to capture sound from multiple sound source locations of an outside sound field. The outer microphones 105$a$, 105$e$, 105$b$, and 105$f$ work together as the microphone array 105.

In an embodiment, the wearable device 100 is configured as an artificial intelligence (AI)-based headset, herein referred to as an AI headset. The wearable device 100 combines technologies in AI and advanced digital signal processing (DSP), and provides hearing protection, situational awareness, sound identification, clear communication, speech intelligibility, and improved battery life. The wearable device 100 is configured to substantially enhance the performance of personnel in operation and reduce training time. The wearable device 100 also improves personal safety through both hearing protection and improved situational awareness. The wearable device 100 is characterized by multiple functionalities comprising automated sound detection and identification (ID); automated sound localization; automated voice assistance to inform users of the sound ID and sound location or direction; provision of 3D cues in binaural sound to allow users to feel that the sound is coming from an actual direction when wearing the wearable device 100; active noise cancelation (ANC) for hearing protection; intelligent automatic gain control (AGC) for hearing enhancement and hearing protection; background noise reduction (NR); and background noise cancelation using spatial information obtained through beamforming. Background noise reduction comprises reduction of background noise in a recorded sound track over time to improve the signal-to-noise ratio (SNR).

The system comprising the wearable device 100 generates three-dimensional (3D) sound for enhanced situational awareness, such that users can identify the sound source direction or location and acoustic scene. The 3D binaural sound from the wearable device 100 is generated by applying head-related transfer functions (HRTFs) as disclosed in the descriptions of FIG. 3, FIG. 5A, and FIGS. 10A-10B. The system comprising the wearable device 100 also performs sound source localization (SSL) where the microphone array 105 on the wearable device 100 can detect sound source direction in a 3D space. The system comprising the wearable device 100 further performs sound identification (ID) using artificial intelligence to automatically identify multiple sound categories, for example, tank, helicopter, footsteps, propeller airplane, jet, truck, car, gunshots, etc. The system comprising the wearable device 100 further provides voice assistance by combining 3D sound generation, SSL, and sound ID. For example, the wearable device 100 automatically provides voice assistance where a user can hear: " . . . 5 o'clock, gunshot . . . " with a real gunshot sound. The 3D binaural sound allows users to also identify the direction of the gunshot.

Moreover, the system comprising the wearable device 100 facilitates clear two-way communications through noise reduction in both receiving and outgoing signals for supporting and improving both radio and face-to-face communication in the presence or absence of high level continuous or impulsive noise. The system comprising the wearable device 100 performs intelligent automatic gain control (AGC) by automatically increasing gain when the sound is in far-field and too soft for hearing enhancement and reducing the gain when the sound level is too high for hearing protection. The AGC allows a user to hear sound from a distance, thereby enhancing human hearing. The system comprising the wearable device 100 also performs noise reduction by intelligently reducing noise by utilizing the information in both spatial and temporal domains for improving a user's hearing intelligibility. The wearable device 100 also provides passive hearing protection by using selected sound isolation materials for the ear cups 102 and 103. In an embodiment, earplugs are used as an option with the wearable device 100. Furthermore, the system comprising the wearable device 100 performs active noise cancelation (ANC) as disclosed in the description of FIG. 4 and FIG. 11. The system comprising the wearable device 100 is configured for low power consumption. Furthermore, the system comprising the wearable device 100 performs noise monitoring/dosimetry by monitoring and recording noise levels for hearing protection.

Figure 2A:
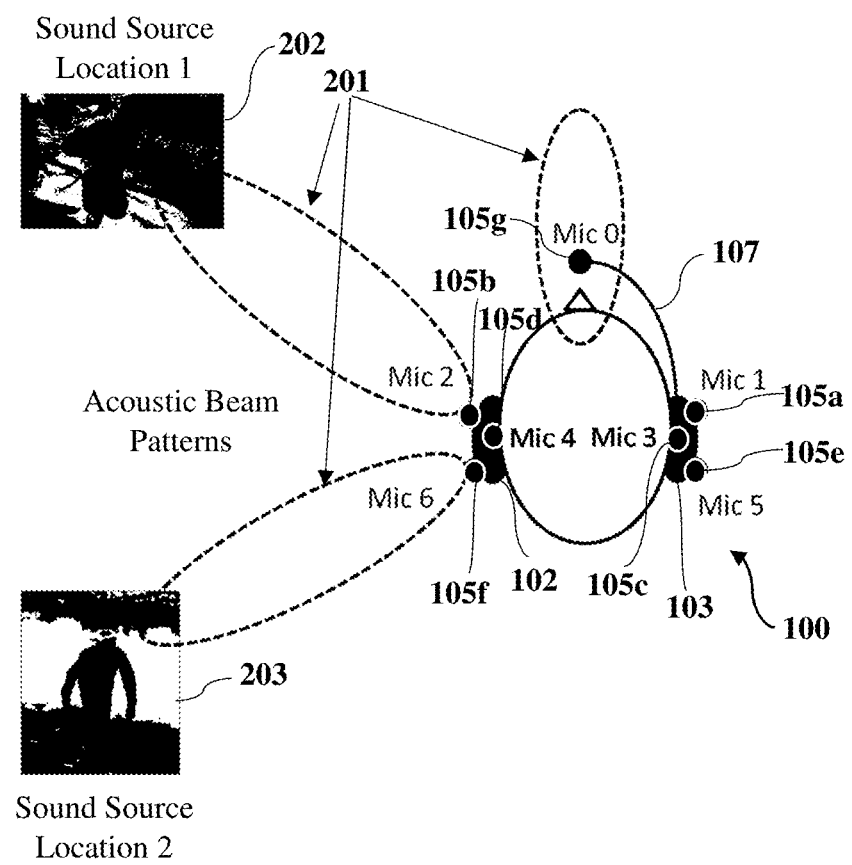
FIG. 2A illustrates a top view of an embodiment of the wearable device for providing situational awareness, showing acoustic beam patterns pointing to different sound source directions.

FIG. 2A illustrates a top view of an embodiment of the wearable device 100 for providing situational awareness, showing acoustic beam patterns 201 pointing to different sound source directions. As illustrated in FIG. 2A, the microphone array 105 comprises two outer microphones 105b and 105f disposed on the left ear cup 102 of the wearable device 100 and two microphones 105a and 105e disposed on the right ear cup 103 of the wearable device 100. FIG. 2A also illustrates two inner microphones 105c and 105d disposed inside the right ear cup 103 and the left ear cup 102, respectively, and configured for active noise cancelation. When the outside noise level is high, for example, above 85 decibels (dB), and passive protection is insufficient, the inner microphones 105c and 105d capture the sound inside the ear cups 103 and 102, respectively, and actively generate an inverse signal to cancel the loud sound, respectively, for each of the ear cups 103 and 102. In an embodiment, a supplementary microphone 105g, for example, a boom microphone, is operably coupled to an adjustable arm 107 extending from one of the ear cups, for example, the right ear cup 103 as illustrated in FIG. 2A. The supplementary microphone 105g is configured to allow a user to speak thereinto for facilitating two-way communications, for example, a face-to-face communication and a radio communication.

Figure 3:
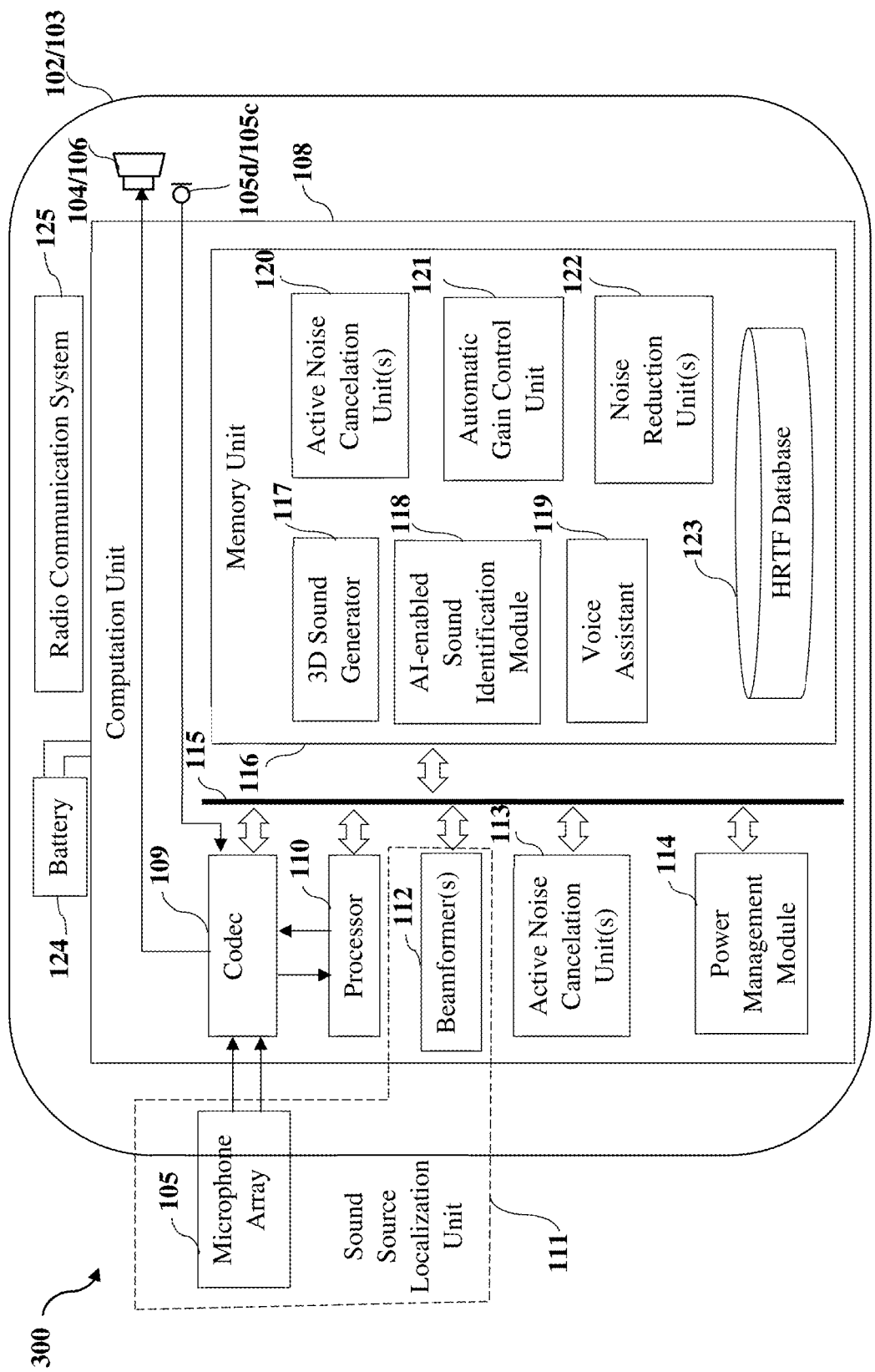
FIG. 3 illustrates an architectural block diagram of an exemplary implementation of a computation unit of a system for providing hearing protection and situational awareness.

Since the microphone array 105 comprises multiple microphones, for example, 105a, 105e, 105b, and 105f, differences of sound arrival time between microphone components are used for forming acoustic beam patterns 201 and then estimating locations of sources of the sounds, herein referred to as "sound source locations", and sound contents in a corresponding sound source direction from an output sound of a corresponding acoustic beam pattern. FIG. 2A indicates two sound source locations 202 and 203. The sources of the sounds, herein referred to as "sound sources", in a training or operational scenario comprise, for example, vehicles, airplanes, tanks, helicopters, gunshots, footsteps, etc. One or more beamformers 112, which are incorporated in the wearable device 100 as illustrated in FIG. 3, generate acoustic beam patterns 201 pointing to different sound source directions and facilitate generation of the 3D binaural sound as disclosed in the descriptions of FIGS. 3-4, FIGS. 8-9, and FIGS. 10A-10B. The acoustic beam patterns 201 formed around the microphones 105b, 105f, and 105g are illustrated in FIG. 2A. The beamformer(s) 112 and the microphone array 105 together constitute a sound source localization unit 111 of the system 300 as illustrated in FIG. 3. The sound source localization unit 111 is operably coupled to the ear cups 102 and 103 of the wearable device 100. The sound source localization unit 111 performs beamforming and sound source localization using the microphone array 105 comprising the outer microphones 105a, 105e, and 105b, 105f disposed in both the ear cups 103 and 102, respectively. Each beamformer 112 is configured to generate one or more acoustic beam patterns 201 pointing to one or more sound source directions as illustrated in FIG. 2A.

The sound in a particular direction of an acoustic beam pattern, herein referred to as a "beam pattern direction", comprises the sound of the sound source in that particular beam pattern direction and background noise from other directions. To further enhance a signal-to-noise ratio (SNR) in the particular beam pattern direction, that is, to only output the sound of the sound source in the particular beam pattern direction, the sound from other acoustic beam patterns that constitutes spatial information is used to cancel the other sound captured in the particular acoustic beam pattern, thereby obtaining an output containing only the sound from the particular beam pattern direction.

Figure 2B:
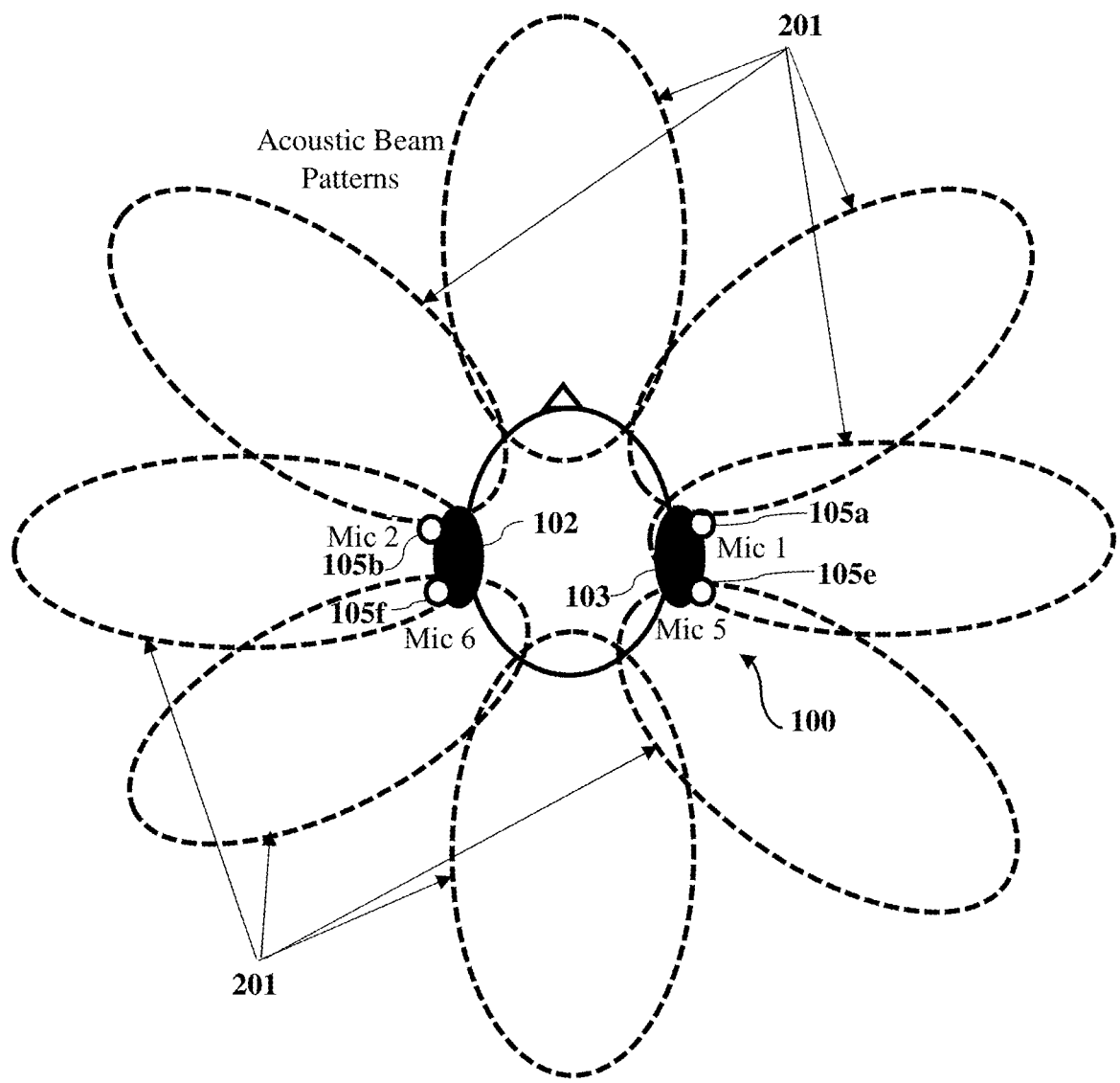
FIG. 2B illustrates a top view of an embodiment of the wearable device, showing acoustic beam patterns of a microphone array on the wearable device.

FIG. 2B illustrates a top view of an embodiment of the wearable device 100, showing acoustic beam patterns 201 of the microphone array 105 on the wearable device 100. The system 300 implemented in the wearable device 100 and comprising the sound source localization unit 111 constituted by the microphone array 105 and the beamformer(s) 112, and a computation unit 108 as illustrated in FIG. 3, implements a three-dimensional (3D) sound technology for converting sound captured by the microphone array 105 comprising the outer microphones 105b and 105f disposed at outer locations of the left ear cup 102 and the outer microphones 105a and 105e disposed at outer locations of the right ear cup 103, into 3D binaural sound, instead of conventional stereo sound. The 3D sound comprises cues of spatial information and cues of individual sound source directions, thereby allowing a listener to perceive different sound from different directions as illustrated in FIG. 2A. 3D binaural sound is the 3D sound in a two-channel, left and right, format. The computation unit 108, in communication with the sound source localization unit 111, generates the 3D sound, and in turn, the 3D binaural sound, as disclosed in the description of FIG. 3 and FIGS. 10A-10B. In an embodiment, signal processing modules of the computation unit 108 are implemented in one of the ear cups 102 and 103 of the wearable device 100 to support all computations. In another embodiment, the signal processing modules of the computation unit 108 are implemented in both of the ear cups 102 and 103 of the wearable device 100. In another embodiment, one or more of the signal processing modules of the computation unit 108 are implemented in one or more of the ear cups 102 and 103 of the wearable device 100. The computation unit 108, in communication with the sound source localization unit 111, uses one or multiple acoustic beam patterns 201 to enhance the sound coming from one beam pattern direction while canceling the sound coming from outside the beam pattern direction. The generated 3D sound and in turn the 3D binaural sound allow users of the wearable device 100 to feel the sound as if the sound is coming from real 3D space, thereby substantially improving situational awareness for users such as warfighters, first responders, game players, etc. The system 300 implemented in the wearable device 100 provides ambient sound along with cues of sound source directions to a user through left and right speakers 104 and 106, respectively, illustrated in FIGS. 1A-1B. The wearable device 100 allows the user wearing the wearable device 100 to hear enhanced speech and/or target sounds around the user in noisy environments and be able to identify directions and locations of one or more target sounds, for example, gunshots, in operations, training, gaming, etc.

FIG. 3 illustrates an architectural block diagram of an exemplary implementation of the computation unit 108 of the system 300 for providing hearing protection and situational awareness. The system 300 disclosed herein is implemented in the wearable device 100, for example, a headset, comprising hearing members, for example, ear cups 102 and 103 as illustrated in FIGS. 1A-1B, configured to be worn on a user's left and right ears. In an embodiment, the system 300 comprises an independent radio communication system 125 disposed in one or more of the ear cups 102 and 103 of the wearable device 100. The radio communication system 125 is configured to operate even when the wearable device 100 is switched off. FIG. 3 illustrates an implementation of the computation unit 108 in either one of the ear cups 102 and 103 to support the computations of the system 300. In an embodiment, the computation unit 108 is disposed in one of the ear cups 102 and 103. The computation unit 108 is operably coupled to the inner microphone 105d/105c and to the microphone array 105 comprising all the outer microphones 105a, 105e and 105b, 105f disposed in the ear cups 103 and 102 of the wearable device 100, respectively, illustrated in FIGS. 1A-1B. One or more printed circuit boards (not shown) are disposed in each of the ear cups 102 and 103 for mounting and interconnecting electronic components, for example, the speakers 104 and 106, the inner microphones 105d and 105c, and the computation unit 108 of the system 300. Furthermore, in an embodiment, a battery 124, for example, an AA battery, is operably coupled to the computation unit 108 with a balance of weight, for powering the computation unit 108. In an embodiment, the computation unit 108 comprises a power management module 114 configured to manage the distribution of power from the battery 124, within the computation unit 108. Through the power management module 114, the computation unit 108 consumes less power from the battery 124 used to power the wearable device 100, thereby allowing use of the battery 124 for an extended period of time.

In an optional embodiment, the computation unit 108 further comprises a coder-decoder (codec) 109 operably coupled to the microphone array 105 and the inner microphone 105d/105c. The codec 109 comprises an analog-to-digital converter (ADC) and a digital-to-analog converter (DAC) in a single unit. The ADC in the codec 109 converts analog audio signals, that is, the sound captured by the microphone array 105, into digital audio signals for transmission and processing. In an embodiment, the codec 109 also encodes the analog audio signals for storage in a digital format. The codec 109 is also operably coupled to the speaker 104/106 in the corresponding ear cup 102/103 for driving the speaker 104/106 in a running mode of the wearable device 100. The DAC in the codec 109 decompresses and converts processed and stored digital data into an analog signal which reaches a user's ear through the speaker 104/106. In the running mode, the communication channels, including one boom microphone 105g disposed close to the user's mouth when the user wears the wearable device 100 on the user's head as illustrated in FIG. 2A, and the two speakers 104 and 106, are enhanced with noise reduction ensuring clear communication. Noise reduction is the process of reducing background noise in an audio channel based on temporal information comprising, for example, statistical properties between signal and noise or frequency distributions of different types of signals. When the system 300 is powered off, the boom microphone 105g and the speakers 104 and 106 operate independently and bypass the computation unit 108 with the codec 109, as a common headset with radio.

The computation unit 108 further comprises at least one processor 110 and a memory unit 116 operably and communicatively coupled to the processor(s) 110. The processor(s) 110 refers to one or more microprocessors, central processing unit (CPU) devices, finite state machines, computers, microcontrollers, digital signal processors, logic, a logic device, an application specific integrated circuit (ASIC), a field-programmable gate array (FPGA), a chip, etc., or any combination thereof, capable of executing computer programs or a series of commands, instructions, or state transitions. In an embodiment, the processor(s) 110 is implemented as a processor set comprising, for example, a programmed microprocessor and a math or graphics co-processor. The computation unit 108 utilizes one or more ultra-low power processors for executing computer program instructions. In an embodiment, the computation unit 108 is configured as a microcontroller, where the memory unit 116 is a program memory that stores instructions of the algorithms of the computation unit 108, and the processor 110 is a central processing unit (CPU) that executes the instructions. In this embodiment, the computation unit 108 is a microcontroller unit (MCU) configured to function as a processor of the system 300 and performs most of the computations. In another embodiment, the computation unit 108 is configured as a digital signal processor (DSP), where the memory unit 116 is a program memory that stores instructions of the algorithms of the computation unit 108, and the processor 110 is a DSP core that executes the instructions. In an embodiment, the algorithms can be stored in an external memory such as an external flash memory or a static random-access memory (SRAM), and executed by the CPU of the microcontroller or the DSP core.

The memory unit 116 is a non-transitory, computer-readable storage medium configured to store computer program instructions defined by multiple signal processing modules, for example, 117, 118, 119, 120, 121, 122, etc., of the computation unit 108. As used herein, "non-transitory, computer-readable storage medium" refers to all computer-readable media that contain and store computer programs and data. The memory unit 116 serves as a storage unit for recording, storing, and reproducing data, computer program instructions, and applications. In an embodiment, the memory unit 116 comprises a random-access memory (RAM) or another type of dynamic storage device that serves as a read and write internal memory and provides short-term or temporary storage for information and computer program instructions executable by the processor(s) 110. The memory unit 116 also stores temporary variables and other intermediate information used during execution of the computer program instructions by the processor(s) 110. In another embodiment, the memory unit 116 further comprises a read-only memory (ROM) or another type of static storage device that stores firmware, static information, and computer program instructions for execution by the processor(s) 110. In an embodiment, the signal processing modules, for example, 117, 118, 119, 120, 121, 122, etc., of the computation unit 108 are stored in the memory unit 116. In an embodiment, the memory unit 116 is configured to store a built-in database 123 of head-related transfer function (HRTF) filters. HRTF filters are DSP filters that are used to simulate an acoustic effect of sound waves as the sound waves pass through the human head and reach the ears. As sound strikes a user, the size and shape of the user's head, ears, ear canal, density of the head, size and shape of nasal and oral cavities, etc., all modify the sound and affect how the sound is perceived, boosting some frequencies and attenuating other frequencies. The HRTF filters mathematically characterize the modifications incurred by sound waves due to the shape of the head, the ears, the torso, etc., as the sound waves propagate through the air. In an embodiment, the HRTF filters are used as a pair of DSP filters, one for each ear, and are applied to a digital audio signal to create a sense of spatialization and three-dimensional (3D) sound. For each beam pattern output or sound source, a 3D sound generator 117 of the system 300 applies a pair of HRTF filters to the sound captured by the microphone array 105 to generate a 3D binaural sound for left and right ears, which represents the sound from that beampattern or sound source direction. The computation unit 108 further comprises a data bus 115 configured to permit communications and exchange of data between the components, for example, 109, 110, 111, 113, 114, and 116 of the computation unit 108.

The processor(s) 110 is configured to execute the computer program instructions defined by the signal processing modules, for example, 117, 118, 119, 120, 121, 122, etc., of the computation unit 108. The signal processing modules, for example, 117, 118, 119, 120, 121, 122, etc., of the computation unit 108, when loaded into the memory unit 116 and executed by the processor(s) 110, implement the computation unit 108 as a programmed, computing device configured to execute the functionality disclosed herein for hearing protection and situational awareness. The processor(s) 110 receives the digital audio signals converted by the codec 109 and processes the digital audio signals using the computer program instructions defined by the signal processing modules, for example, 117, 118, 119, 120, 121, 122, etc., and stored in the memory unit 116.

Figure 4:
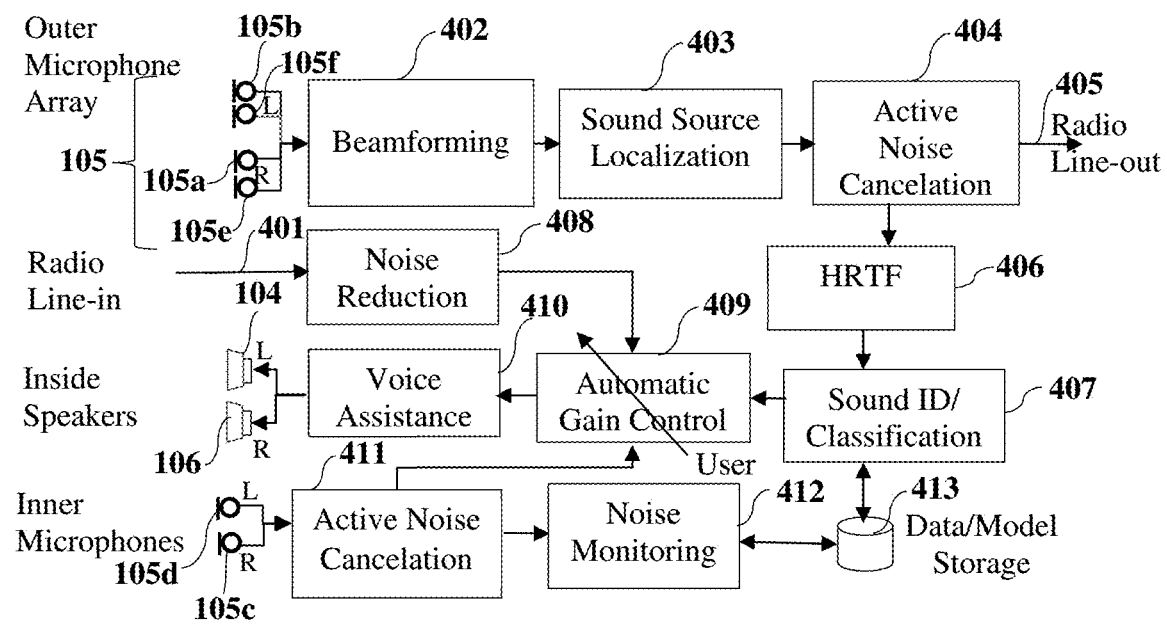
FIG. 4 illustrates a block diagram of an exemplary software implementation of the system for providing hearing protection and situational awareness.
Figure 10A:
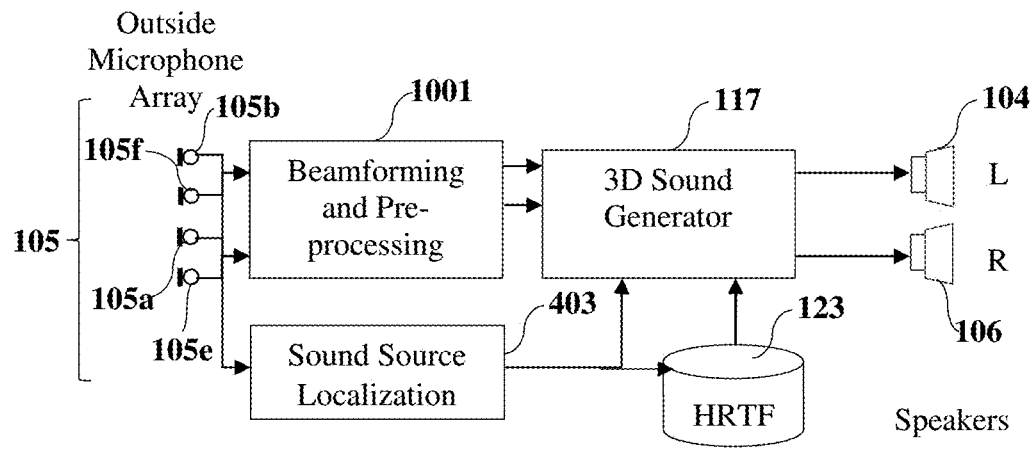
FIG. 10A illustrates a block diagram showing an embodiment of generating three-dimensional binaural sound using acoustic beamforming, sound source localization, and head-related transfer functions.

The sound source localization unit 111 of the system 300 is configured to perform sound source localization (SSL) 403 as disclosed in the description of FIG. 4 and FIG. 10A. In an embodiment, the sound source localization unit 111 performs SSL by distinguishing the time difference of the target sound arriving at the outer microphones, for example, 105b, 105f, 105a, and 105e, of the microphone array 105. By using two outer microphones 105b, 105f and 105a, 105e on each of the ear cups 102 and 103, respectively, to form the microphone array 105, the sound source localization unit 111 achieves full 360-degree situational awareness. Since the four outer microphones 105b, 105f and 105a, 105e are on a plane, a direction can be uniquely determined by a time difference of arrival (TDOA) of four receivers, if they are not forming a line. The sound source localization unit 111 is configured to execute any suitable sound source localization algorithm based on the microphone layout and the computational capability of the processor(s) 110. In an embodiment, the sound source localization unit 111 comprises one or more beamformers 112 and the microphone array 105. Each beamformer 112 is configured to generate one or more acoustic beam patterns pointing to one or more sound source directions. Each beamformer 112 operates together with the microphone array 105 on the ear cups 102 and 103 to generate one or more acoustic beam patterns. One beamformer 112 comprises one set of filter parameters to form one acoustic beam pattern. The microphone array 105 is configured to capture sound from at least one of the sound source directions of the acoustic beam patterns, outside of the ear cups 102 and 103. Each beamformer 112 is configured to output a sound track. Each sound track is associated with the captured sound in a particular sound source direction(s) of the acoustic beam pattern(s).

The signal processing modules of the computation unit 108 comprise a 3D sound generator 117. For each beamformer 112, the 3D sound generator 117 retrieves a pair of HRTF filters associated with the sound source direction(s) of the acoustic beam pattern(s) generated by each beamformer 112, from the database 123. In an embodiment, one or more HRTF filters are selected from the database 123 based on one or more relative positions or directions of the sound sources and the direction that the user faces in a 3D space as disclosed in Applicant's non-provisional patent application titled "Three-dimensional Audio Systems", filed on Apr. 9, 2021, now issued as U.S. Pat. No. 11,240,621. In another embodiment, a pair of HRTF filters associated with one acoustic beam pattern is selected from the database 123. The 3D sound generator 117 applies the retrieved pair of HRTF filters to the output sound track from each beamformer 112, to generate two filtered sound tracks for the left ear and the right ear, respectively. Each of the two filtered sound tracks represents the sound captured from the particular sound source direction(s) of the acoustic beam pattern(s) and comprises a cue of the particular sound source direction(s). The 3D sound generator 117 combines the filtered sound tracks generated for the left ear into a left sound channel to drive the speaker(s) 104 in the left ear cup 102 of the wearable device 100, and combines the filtered sound tracks generated for the right ear into a right sound channel to drive the speaker(s) 106 in the right ear cup 103 of the wearable device 100, thereby generating a 3D binaural sound comprising cues of the sound source directions. The speakers 104 and 106 in the ear cups 102 and 103 of the wearable device 100, respectively, reproduce real sound outside of the wearable device 100.

In an embodiment, the signal processing modules further comprise an artificial intelligence (AI)-enabled sound identification module 118 configured to automatically decode and recognize characteristics of the captured sound and identify categories of the captured sound using one or more pretrained AI models as disclosed in the descriptions of FIGS. 5A-7B. The AI-enabled sound identification module 118 executes one or more AI-based algorithms, models, methods, etc., to automatically recognize characteristics of the captured sound and identify categories of the captured sound. The AI-enabled sound identification module 118 executes speech recognition and speaker identification technology for sound identification. The AI-enabled sound identification module 118 utilizes acoustic models that are trained with different types of sound, to decode the captured sound. The system 300 with the AI-enabled sound identification module 118 is herein referred to as an "AI-based system". In an embodiment, the signal processing modules further comprise a voice assistant 119 operably coupled to the speaker 104/106. The voice assistant 119, in communication with the AI-enabled sound identification module 118 and the sound source localization unit 111, is configured to determine one or more sound source locations from the output sound track of each beamformer 112 and to report the identified categories of the captured sound and a direction or location of the captured sound with voice assistance via the speaker 104/106 as disclosed in the description of FIG. 5A-5B. In an embodiment, the voice assistant 119, in communication with the AI-enabled sound identification module 118 and the sound source localization unit 111, is configured to report the identified categories of the captured sound and a location of the captured sound with voice assistance via one or more interface devices comprising, for example, a graphical user interface (GUI).

Figure 11:
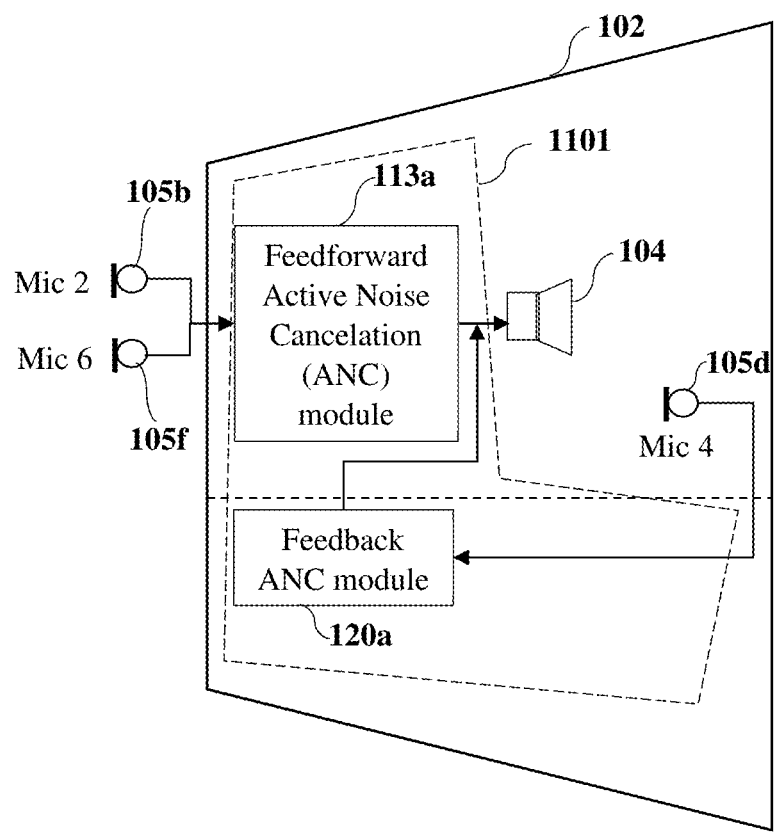
FIG. 11 illustrates a block diagram of an embodiment of an active noise cancelation unit implemented in one of the hearing members of the wearable device.

In an embodiment, the signal processing modules further comprise one or more active noise cancelation (ANC) units 120 configured to cancel noise above a predetermined threshold level, for example, about 85 dB, captured by one or more of the inner microphones 105d and 105c and to cancel background noise captured by the microphone array 105, for improving hearing protection as disclosed in the description of FIG. 11. That is, the ANC unit(s) 120 cancels background noise above a predetermined threshold level, captured by the inner microphone 105d/105c and/or the microphone array 105, for providing hearing protection through the ear cup 102/103.

In another embodiment, the computation unit 108 further comprises one or more supplementary ANC units 113 configured to operate when the noise level is substantially high for hearing protection. The supplementary ANC unit(s) 113 is operably coupled to the microphone array 105 and the beamformer(s) 112. For the output sound track of each beamformer(s) 112, the supplementary ANC unit(s) 113 is configured to cancel noise that is obtained from sound in other one or more output sound tracks of the other beamformers, from the output sound track, thereby enhancing the sound from the particular sound source direction(s) of the acoustic beam pattern(s) and reducing the noise from the other sound source directions to improve the signal-to-noise ratio (SNR). The supplementary ANC unit(s) 113, therefore, cancels noise from all other acoustic beam pattern directions of other beamformers to improve the SNR of one beamformer 112. This is because the output of each beamformer 112 comprises noise from other directions. The supplementary ANC unit(s) 113 repeats this noise cancelation for all beamformers, one by one. The supplementary ANC unit(s) 113 cancels the noise obtained from sound that is combined by other output sound tracks of corresponding beamformers. The supplementary ANC unit(s) 113 uses the sound from all other beamformers to cancel the noise in one beamformer output, thereby improving the SNR of the output of that one beamformer 112. The supplementary ANC unit(s) 113, therefore, uses spatial information to perform noise cancelation. In another embodiment, the signal processing modules further comprise an automatic gain control unit 121 configured to control a level of output sound of the speaker 104/106 by selectively increasing gain when a level of the output sound is substantially low for hearing enhancement and situational awareness, and reducing the gain when the level of the output sound is substantially high for hearing protection as disclosed in the description of FIG. 13. The automatic gain control unit 121 is configured to distinguish an autocorrelation of an audio signal associated with the captured sound to an uninformative noise. In an embodiment, the signal processing modules further comprise one or more noise reduction units 122 configured to reduce noise in incoming audio signals and outgoing audio signals for improving the SNR in two-way communications comprising, for example, face-to-face communication and radio communication. In an embodiment, the noise reduction unit(s) 122 executes a noise reduction algorithm based on statistical analysis for reducing noise in incoming audio signals and outgoing audio signals for enhancing two-way communications. In another embodiment, the noise reduction unit(s) 122 executes a noise reduction algorithm based on modeling of audio signals for reducing noise in incoming audio signals and outgoing audio signals for enhancing two-way communications.

In various embodiments, in addition to the 3D sound generator 117, the computation unit 108 of the system 300 comprises one or more of the other signal processing modules, for example, 118, 119, 120, 121, and 122 disclosed above in different combinations. For example, in an embodiment, the computation unit 108 comprises the 3D sound generator 117 and other signal processing modules, namely, the active noise cancelation (ANC) unit(s) 113/120 and the automatic gain control unit 121. In another embodiment, the computation unit 108 comprises the 3D sound generator 117 and other signal processing modules, namely, the AI-enabled sound identification module 118 and the voice assistant 119. In another embodiment, the computation unit 108 comprises the 3D sound generator 117 and other signal processing modules, namely, the AI-enabled sound identification module 118, the voice assistant 119, the ANC unit(s) 113/120, and the automatic gain control unit 121.

The processor(s) 110 retrieves instructions defined by the 3D sound generator 117, the AI-enabled sound identification module 118, the voice assistant 119, the active noise cancelation unit(s) 120, the automatic gain control unit 121, and the noise reduction unit(s) 122 from the memory unit 116 for executing the respective functions disclosed above. The signal processing modules 117, 118, 119, 120, 121, 122, etc., of the computation unit 108 are disclosed above as software executed by the processor(s) 110. In an embodiment, the signal processing modules 117, 118, 119, 120, 121, 122, etc., of the computation unit 108 are implemented completely in hardware. In another embodiment, the signal processing modules 117, 118, 119, 120, 121, 122, etc., of the computation unit 108 are implemented by logic circuits to carry out their respective functions disclosed above. In another embodiment, the computation unit 108 is also implemented as a combination of hardware and software including one or more processors, for example, 110, that are used to implement the signal processing modules, for example, 117, 118, 119, 120, 121, 122, 123, etc., of the computation unit 108.

A module or a unit, as used herein, refers to any combination of hardware, software, and/or firmware. As an example, a module or a unit includes hardware such as a microcontroller associated with a non-transitory, computer-readable storage medium to store computer program codes adapted to be executed by the microcontroller. Therefore, references to a module or a unit, in an embodiment, refer to the hardware that is specifically configured to recognize and/or execute the computer program codes to be held on a non-transitory, computer-readable storage medium. In an embodiment, the computer program codes comprising computer readable and executable instructions are implemented in any programming language, for example, C, C++, C #, Java®, Perl®, Python®, Objective-C®, MATLAB® of The MathWorks, Inc., etc. In another embodiment, other object-oriented, functional, scripting, and/or logical programming languages are also used. In an embodiment, the computer program codes or software programs are stored on or in one or more mediums as object code. In another embodiment, the term "module" or "unit" refers to the combination of the microcontroller and the non-transitory, computer-readable storage medium. Often module or unit boundaries that are illustrated as separate commonly vary and potentially overlap. For example, a module or a unit may share hardware, software, firmware, or a combination thereof, while potentially retaining some independent hardware, software, or firmware. In various embodiments, a module or a unit includes any suitable logic.

FIG. 4 illustrates a block diagram of an exemplary software implementation of the system 300 shown in FIG. 3, for providing hearing protection and situational awareness. The sound source localization unit 111, the artificial intelligence (AI)-enabled sound identification module 118, the voice assistant 119, the active noise cancelation (ANC) units 113 and 120, the automatic gain control (AGC) unit 121, and the noise reduction unit(s) 122 of the system 300 illustrated in FIG. 3, execute multiple digital signal processing functions comprising, for example, beamforming 402/sound source localization 403, sound identification/classification 407, voice assistance 410, active noise cancelation 404, automatic gain control 409, and noise reduction 408, respectively, as illustrated in FIG. 4. In an embodiment, the digital signal processing (DSP) functions of the computation unit 108 illustrated in FIG. 3, are implemented in software. The ANC unit 120 executes active noise cancelation 411, while the inner microphones 105d and 105c execute a noise monitoring function 412. The ANC unit 120 executes active noise cancelation 411 to cancel background noise that leaks into the ear cups 102 and 103 illustrated in FIGS. 1A-1B. The ANC unit 120 uses the inner microphones 105d and 105c to capture the leaked background noise and then uses the captured background noise to cancel the leaked background noise in the sound channels driving the speakers 104 and 106 illustrated in FIGS. 1A-1B. The ANC unit 120 is activated when the noise level is above a predetermined threshold and in this case, does not cancel target sound. For example, as the sound of footsteps is soft, the ANC unit 120 does not cancel the sound of footsteps, but instead enhances the sound of footsteps.

The beamformer(s) 112 of the sound source localization unit 111 illustrated in FIG. 3, performs beamforming 402 and forms acoustic beam patterns pointing to the sound source. The acoustic beam patterns enhance the sound from the direction of that sound source and improve the signal-to-noise ratio (SNR) and hearing intelligibility. The sound source localization unit 111 comprising the microphone array 105 and the beamformer(s) 112 performs sound source localization 403 to detect a direction of a sound source. Since the sound arrival time to each of the four outer microphones 105b, 105f, 105a, and 105e of the microphone array 105 is different, the sound source localization unit 111 uses this sound arrival time difference information to detect the direction of the sound source. The active noise cancelation (ANC) unit 113 utilizes spatial information from the microphone array 105 to cancel the sound from other directions. The ANC unit 113 performs active noise cancelation 404 to cancel noise arriving from outside the acoustic beam patterns formed by the beamformer(s) 112. In an embodiment, as each sound track of an associated acoustic beam pattern contains noise or sound from other directions, the ANC unit 113 uses the sound from other sound tracks, which constitutes spatial information, to cancel the noise or sound from other directions, thereby enhancing the sound from the direction of the associated acoustic beam pattern and reducing the noise or sound from other directions to improve the SNR. In this embodiment, the noise reduction unit(s) 122 performs noise reduction 408 using the spatial information. In another embodiment, for each sound track, the ANC unit 113 applies models or filters to reduce the background noise, thereby using temporal information for noise reduction 408. The enhanced line-level audio signals that are output from the ANC unit 113 are passed through a radio line-out port 405. The beamformer(s) 112, after beamforming 402, generates two outputs, that is, sound location and enhanced single channel audio.

The three-dimensional (3D) sound generator 117 of the computation unit 108 illustrated in FIG. 3, then uses the sound location information received from the beamformer(s) 112 to retrieve the corresponding head-related transfer function (HRTF) filters 406 from a bank of HRTF filters, that is, from the HRTF database 123 illustrated in FIG. 3. The 3D sound generator 117 uses the HRTF filters to process the output of the microphone array 105 to generate two channels, that is, a left sound channel and a right sound channel, as binaural audio. The binaural signal allows a user wearing the wearable device 100 illustrated in FIGS. 1A-1B, to localize sound direction similar to how human ears and brain localize sound direction. The 3D sound generator 117 combines the HRTF outputs for the left ear and the right ear to generate a left sound channel and a right sound channel for a left speaker 104 and a right speaker 106, respectively. By generating 3D binaural sound and providing voice assistance 410, the wearable device 100 disclosed herein retains vital sound direction information, which enhances situational awareness and improves personal safety of the user.

As disclosed above, the beamformer(s) 112 forms an acoustic beam pattern pointing to the sound source. In an embodiment, the beamformer(s) 112 executes a fixed beamforming algorithm for forming the acoustic beam patterns. By executing a fixed beamforming algorithm, the beamformer(s) 112 forms multiple acoustic beam patterns and continues computations using signals from the microphones 105b, 105f, 105a, and 105e of the microphone array 105. The beamformer(s) 112 is configured to determine which specific acoustic beam pattern or which specific combination of acoustic beam patterns are to be passed to the signal processing modules. In another embodiment, the beamformer(s) 112 executes a non-fixed beamforming algorithm for forming the acoustic beam patterns. By executing the non-fixed beamforming algorithm, the sound source localization unit 111 determines how the microphone array 105 will be steered, based on different arrival times of sound to each of the microphones 105b, 105f, 105a, and 105e of the microphone array 105.

The outer microphones 105b, 105f, 105a, and 105e are not limited for use as a microphone array 105. In an embodiment, the outer microphones 105b, 105f, 105a, and 105e also constitute a microphone array 105 for active noise cancelation (ANC) processing. Moreover, for noise reduction 408 and speech enhancement for both face-to-face communication and radio communication, the outer microphones 105b, 105f, 105a, and 105e are configured as reference microphones for collecting ambient noise. Furthermore, noise as a sound wave arrives at the outer microphones 105b, 105f, 105a, and 105e earlier than arrival at the user's ears, therefore some reactions such as increasing the ANC level or muting the speakers 104 and 106 to protect the user, can be determined from the signals from these outer microphones 105b, 105f, 105a, and 105e.

The beamforming/sound source localization output feeds to the AI-enabled sound identification module 118. The AI-enabled sound identification module 118 is configured to recognize the sound characteristics and identify the sound categories, for example, voice, gunshot, airplane, helicopter, tank, truck, footsteps, etc., using pretrained AI models and AI-based algorithms. The AI-enabled sound identification module 118 applies a trained machine learning model stored in a data/model storage database 413 to the beamforming output for identifying the sound categories. In an embodiment, the AI-enabled sound identification module 118 stores the identified sound categories and associated data in the data/model storage database 413 for further training the machine learning model. In an embodiment, the AI-enabled sound identification module 118 reports the identified sound categories to the user using a pre-recorded voice for voice assistance 410.

Furthermore, the inner microphones 105c and 105d illustrated in FIG. 4, capture the sound arriving close to the user's ear canal. When the sound level is high through the ear cups 102 and 103 illustrated in FIGS. 1A-1B, for example, from helicopter noise, the active noise cancelation (ANC) unit 120 is activated automatically as disclosed in the description of FIG. 11. The ANC unit 120 generates anti-noise with an inversed phase to cancel the high-level sound to further promote noise attenuation, and to protect the user's hearing. The ANC unit 120, therefore, performs active noise cancelation 411 to cancel noise that arrives inside the ear cups 102 and 103. Input audio signals from a radio line-in port 401 of the wearable device 100 undergo noise reduction 408 and automatic gain control 409. The automatic gain control (AGC) unit 121 controls the sound level of playback, such that loud sounds are attenuated to protect hearing, while soft sounds are enhanced for situational awareness. The user may adjust the maximal sound level and maintain the sound level under a threshold for safety. Furthermore, the inner microphones 105c and 105d mounted inside the ear cups 103 and 102 of the wearable device 100, respectively, monitor the sound level inside the wearable device 100, thereby acting as a noise dosimeter. The monitored noise data and the identified sound categories are stored in the data/model storage database 413. In an embodiment, the wearable device 100 comprises a universal serial bus (USB) interface, through which monitored noise data can be retrieved for noise level analysis, hearing protection, and reviewing the user's activities, for example, during training.

Figure 5A:
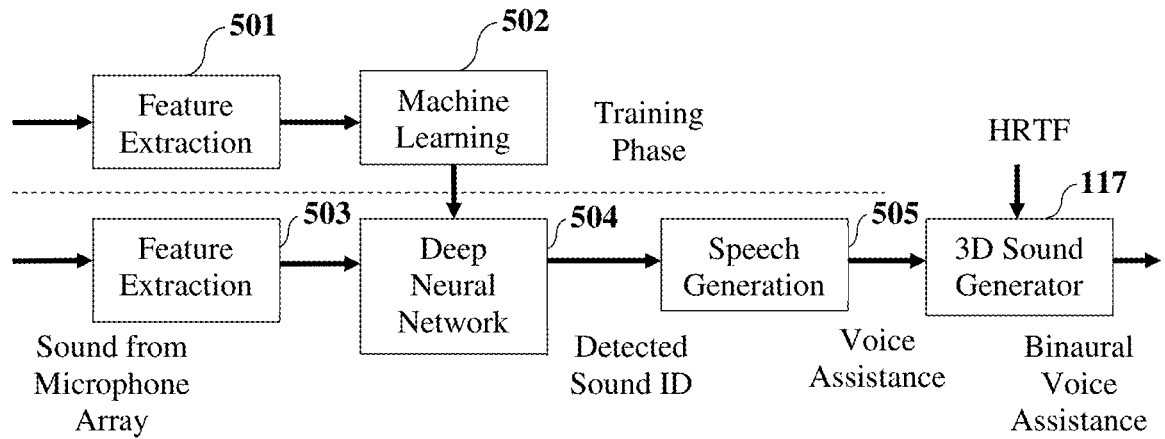
FIG. 5A illustrates a block diagram showing an exemplary implementation of artificial intelligence (AI)-enabled sound identification and voice assistance in an AI-based system.

FIG. 5A illustrates a block diagram showing an exemplary implementation of artificial intelligence (AI)-enabled sound identification and voice assistance in an AI-based system 300 shown in FIG. 3. In an embodiment, the wearable device 100, for example, a headset, of the AI-based system 300 illustrated in FIGS. 1A-1B, is powered by advanced AI technology and is referred to as an "AI headset". In this embodiment, the AI-enabled functions executed by the computation unit 108 illustrated in FIG. 3, comprises automated sound identification (ID) and voice assistance, an overview of which is illustrated in FIG. 5A. The AI-enabled sound identification module 118 and the voice assistant 119 of the computation unit 108 illustrated in FIG. 3, perform automated sound identification and provide voice assistance, respectively. The AI-enabled sound identification module 118 first converts a sound waveform captured by the microphone array 105 illustrated in FIGS. 1A-1B and FIG. 3, into robust auditory-based features through feature extraction 503 by executing an auditory-based feature extraction algorithm. In an embodiment, the AI-enabled sound identification module 118 converts a sound waveform captured by the microphone array 105 into other features used in robust speech recognition using feature extraction 503 based on hearing system signal processing. During training, machine learning technology 502 is applied to train a neural network, for example, a deep neural network (DNN) 504, or a convolutional neural network (CNN), or any efficient neural network, using training data of multiple sound categories comprising, for example, a gunshot, a helicopter sound, a propeller airplane sound, a fixed-wing airplane sound, a tank sound, a truck sound, footsteps, etc. In the training phase, in an embodiment, feature extraction 501 is performed to generate the training data for training the neural network using machine learning 502.

When the microphone array 105 in the wearable device 100 captures sound, the AI-enabled sound identification module 118 performs feature extraction 503 to automatically extract features of the captured sound. Depending on the practical application, usage, and computational resources of the hardware, in an embodiment, the sound identification algorithm executed by the AI-enabled sound identification module 118 comprises a method that uses the features extracted from the captured sound and then categorizes the sound based on a feature domain. In another embodiment as illustrated in FIG. 5A, the sound identification algorithm executed by the AI-enabled sound identification module 118 comprises a neural network-based method, which may not be limited to a particular feature domain for categorization and identification. The AI-enabled sound identification module 118 inputs the extracted features into the trained DNN 504 to identify the categories of the captured sound. After sound identification by the AI-enabled sound identification module 118, the voice assistant 119 performs speech generation 505 and adds voice assistance, based on the results of sound source localization and sound identification, to the captured sound and sends the entire utterance to a corresponding head-related transfer function (HRTF). In an embodiment, the three-dimensional (3D) sound generator 117 generates a 3D binaural sound with voice assistance by applying the HRTF to the output of speech generation 505 executed by the voice assistant 119. As the result, the user wearing the AI headset can hear a 3D binaural sound with voice assistance. Based on the results of sound source localization and sound identification, the voice assistance comprises, for example, a human voice that plays " . . . [gunshot sound] . . . Gunshot at 4 o'clock . . . ". Both the gunshot and voice assistance are in 3D binaural sound.

Figure 5B:
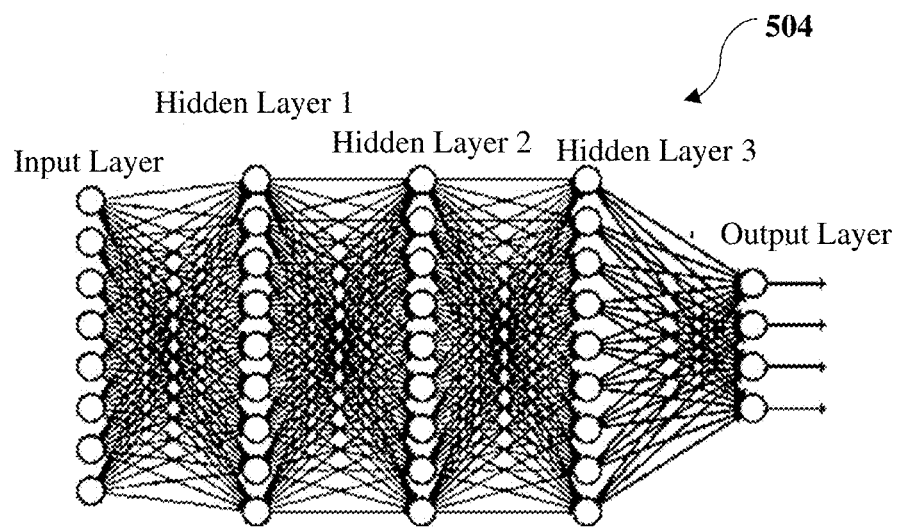
FIG. 5B illustrates an exemplary deep neural network employed in the AI-based system for sound identification.

FIG. 5B illustrates an exemplary deep neural network (DNN) 504 employed in the AI-based system 300 shown in FIG. 3, for sound identification. In an embodiment as illustrated in FIG. 5B, the trained DNN 504 comprises one input layer, three hidden layers, and one output layer. Each of the input and hidden layers comprise 256 nodes. The output layer comprises six nodes, each for one sound category. When a sound category is detected, the corresponding node has an output of 1 and other nodes are zeroes (0 s). After sound identification by the AI-enabled sound identification module 118, the voice assistant 119 illustrated in FIG. 3, performs speech generation 505 and adds voice assistance, based on the results of sound source localization and sound identification, to the captured sound and sends the entire utterance to a corresponding head-related transfer function (HRTF). As a result, a user wearing the wearable device 100 illustrated in FIGS. 1A-1B, hears a three-dimensional (3D) binaural sound with voice assistance, for example: " . . . [gunshot sound] . . . Gunshot at 4 O' clock . . . ".

Figure 6:
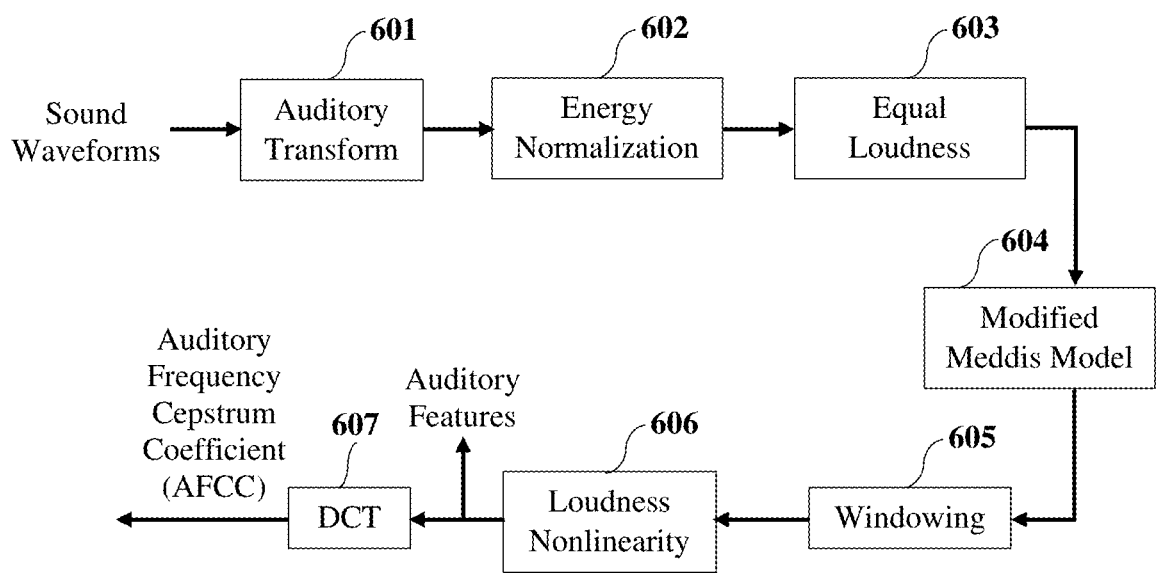
FIG. 6 illustrates a block diagram showing an exemplary implementation of auditory-based feature extraction in the AI-based system for AI-enabled sound identification.

FIG. 6 illustrates a block diagram showing an exemplary implementation of auditory-based feature extraction in the AI-based system 300 shown in FIG. 3, for AI-enabled sound identification. In an embodiment, the AI-enabled sound identification module 118 illustrated in FIG. 3, executes an auditory-based feature extraction algorithm as illustrated in FIG. 6, for automatically recognizing characteristics of the sound captured by the microphone array 105 and identifying categories of the captured sound. The recognized characteristics are robust to background noise and are developed by modeling the human cochlea and auditory neural system. In this embodiment, the feature computation comprises an auditory transform 601 that replaces the Fourier transform, energy normalization 602, an equal loudness function 603, a modified Meddis model 604, windowing 605, loudness nonlinearity 606, and a discrete cosine transform (DCT) function 607 as illustrated in FIG. 6.

An auditory filter bank in the auditory transform 601 simulates the frequency response of a basilar membrane (BM) in the cochlea. Consider f(t) to be any square integrable function. A transform of f(t) with respect to a function representing the BM impulse response $\psi(t)$ is defined as:

$$T(a, b) = \int_{-\infty}^{\infty} f(t) \frac{1}{\sqrt{|a|}} \psi\left(\frac{b-t}{a}\right) dt,$$

where a and b are real, both f(t) and $\psi(t)$ belong to $L^2(R)$, and T(a, b) represents the traveling waves in the BM. The above equation can also be written as follows:

$$T(a,b) = \int_{-\infty}^{\infty} f(t) \psi_{a,b}(t) dt,$$

where $$\psi_{a,b}(t) = \frac{1}{\sqrt{|a|}} \psi\left(\frac{b-t}{a}\right).$$

Factor "a" in the above equations is a scale or dilation variable. By changing "a", the central frequency of an impulse response function can be shifted. Factor "b" in the above equations is a time shift or translation variable. For a given value of "a", factor "b" shifts the function $\psi_{a,0}(t)$ by an amount "b" along the time axis. The auditory filter in the auditory transform 601 is defined as follows:

$$\psi_{a,b}(t) = \frac{1}{\sqrt{|a|}} \left(\frac{b-t}{a}\right)^\alpha \exp\left[-2\Pi f_L \beta\left(\frac{b-t}{a}\right)\right]$$

$$\cos\left[2\Pi f_L\left(\frac{b-t}{a}\right) + \theta\right] u(-t),$$

where $\alpha>0$ and $\beta>0$, u(t) is a unit step function, that is, u(t)=1 for t≥0 and 0 otherwise, and where $\theta$=0. The value of "a" can be determined by the current filter central frequency, $f_c$, and the lowest central frequency, $f_L$, in the auditory filter bank as: $a=f_L/f_c$.

Since $\psi_{a,b}(t)$ is constructed with the lowest frequency along the time axis, the value of "a" is in 0<a≤1. If $\psi$ is stretched, the value of "a" is in a>1. In an embodiment, the frequency distribution of the cochlear filter is in the form of linear or nonlinear scales such as equivalent rectangular bandwidth (ERB). The values of "a" are pre-calculated for all required central frequency of the cochlear filter. The auditory transform 601 generates spectrograms that are free from harmonics, have much less computation noise, and are robust to background noise compared to the spectrograms generated from the Fast Fourier Transform (FFT). In numerical computation, the output of the auditory transform 601 is represented as T (i, n), where "i" represents the number of the frequency band and "t" represents discrete time. Since energy is not being used in the following computation, the gain of the auditory filters in the auditory transform 601 may need to be renormalized. Following the auditory transform 601, the AI-enabled sound identification module 118 applies an equal-loudness function, g(i), to each band of the output of the auditory transform 601 as follows:

$$E(i,n) = g(i)T(i,n) \forall i,n$$

where g(·) is a weighting function on the different frequency bands. In the hearing system, the inner hair cells act to transduce mechanical movements into neural activities. When the basilar membrane moves up and down, a shearing motion is created between the basilar membrane and the tectorial membrane, which causes the displacement of the hairs at the tops of the hair cells which generates the neural signals; however, the hair cells only generate the neural signals in one direction of the basilar membrane movement. When the basilar membrane moves in the opposite direction, there is neither excitation nor neuron output. The AI-enabled sound identification module 118 applies the modified Meddis hair cell model 604 to the computation which includes a feedback loop. The AI-enabled sound identification module 118 applies the following constraints to ensure that the modified Meddis hair cell model output is not negative.

$$M(i, n) = \begin{cases} m[E(i, n)] & \text{if } E(i, n) > 0 \\ 0 & \text{otherwise} \end{cases}$$

where the Meddis model is represented as m(·).

In the next step, the AI-enabled sound identification module 118 converts the hair cell output for each band into a representation of nerve spike count density. The AI-enabled sound identification module 118 performs windowing 605 by using a shifting window to represent the function. The window function with length "l" is represented as:

$$S(i, j) = \frac{1}{l} \sum_{n=n_j}^{n_j+l-1} M(i, n)$$

The window length can be in 20-30 milliseconds (ms) and shifted by 10 ms at each step. Furthermore, the AI-enabled sound identification module 118 applies the scales of a loudness function 606 to the hair cell output as:

$$Y(i,j)=S(i,j)^{1/3}$$

This loudness function 606 implements cubic root non-linearity to model the perceived loudness. In the next step, the AI-enabled sound identification module 118 applies the DCT 607 to decorrelate the feature dimensions and generates the auditory filter cepstral coefficients (AFCCs) as the auditory-based speech features. In a software implementation, the order of the above computation can be changed for fast and efficient computation. Exemplary output features, referred to as the AFCCs, generated by the auditory-based feature extraction algorithm are illustrated in FIG. 7A, for six types of sound.

Figure 7A:
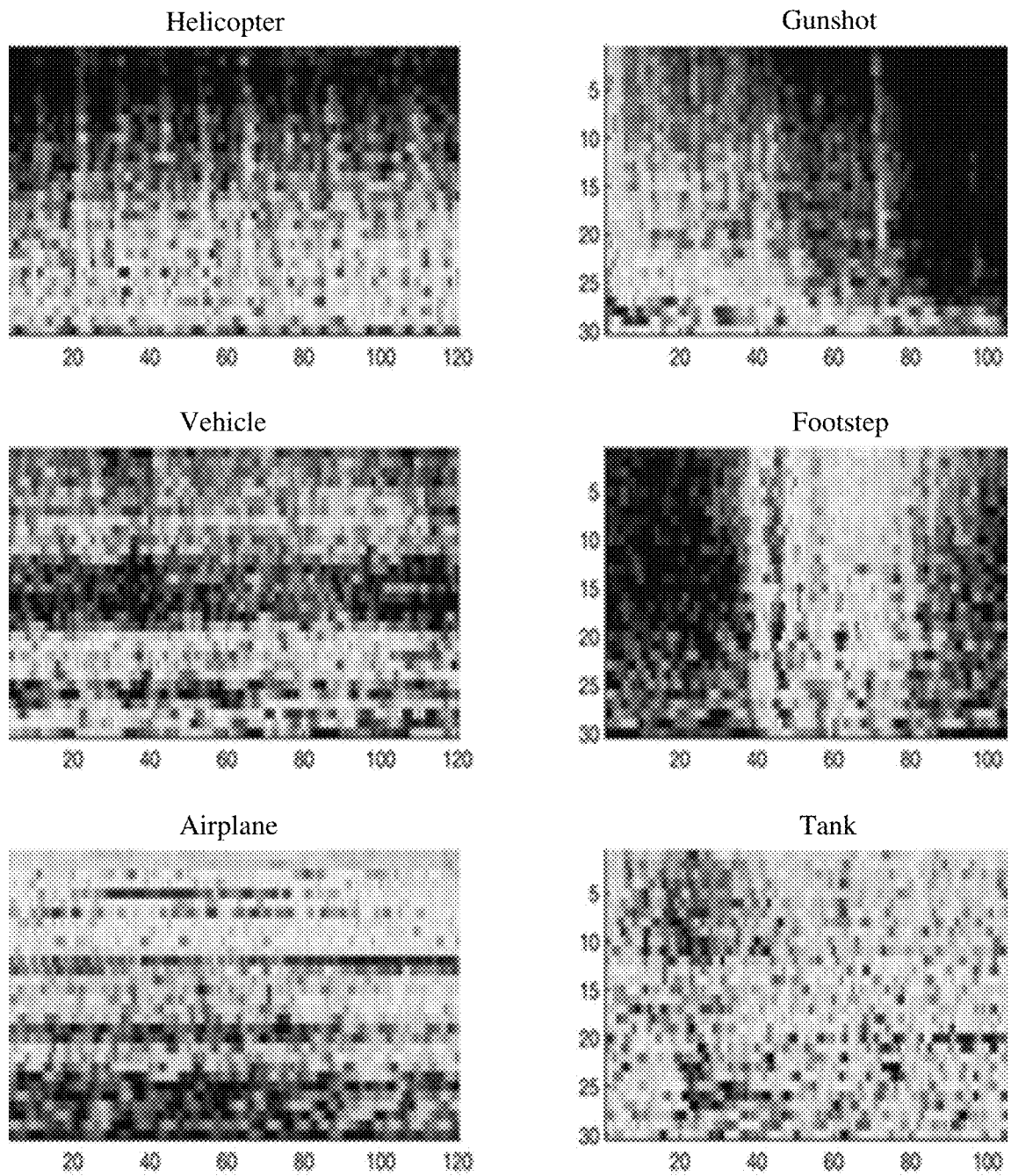
FIG. 7A illustrates exemplary auditory-based spectrograms of sound categories utilized by an AI-enabled sound identification module of the AI-based system for AI-enabled sound identification.

FIG. 7A illustrates exemplary auditory-based spectrograms of sound categories utilized by the AI-enabled sound identification module 118 of the AI-based system 300 shown in FIG. 3, for AI-enabled sound identification. FIG. 7A illustrates auditory-based features from six different sound categories for sound identification, where in an example, 32 frequency bands are distributed as in the cochlea and the time interval is, for example, 10 milliseconds (ms). The sound categories comprise, for example, a helicopter sound, a gunshot, a vehicle sound, a footstep, an airplane sound, and a tank sound as illustrated in FIG. 7A. In an embodiment, the auditory-based features are used to train a neural network, for example, a deep neural network (DNN) 504 with five layers as illustrated in FIG. 5B. Each frame of the features has 32 bands. In an example, ten frames of the features are used to construct a 320-dimensional super vector as the input to the DNN 504. Each hidden layer has 256 nodes while the output layer has 6 nodes, one for each sound class. In an example, during training 50 of 5 second utterances are used for training and another 50 of 5 second utterances are used for testing. A confusion table of evaluation, that is, a confusion matrix, is illustrated in FIG. 7B, using a DNN approach. The average classification accuracy is 99.06%. The testing data performance is close to the above-disclosed accuracy. The AI-enabled sound identification module 118 is configured to be more robust with near perfect accuracy by collecting more data for training and testing.

The AI-enabled sound identification module 118 executes the deep neural network (DNN) 504, which in an embodiment, learned two-dimensional (2D) patterns for identification of the sound categories, also referred to as sound classification. The AI-enabled sound identification module 118 is not limited to executing the above specific algorithm for sound identification. In another embodiment, the AI-enabled sound identification module 118 utilizes different features from those shown in FIG. 7A. In another embodiment, the AI-enabled sound identification module 118 utilizes a Short-Time Fourier Transform (STFT) spectrogram directly for sound identification. In another embodiment, the AI-enabled sound identification module 118 utilizes other different methods of sound classification and identification, which can be DNN-based. In another embodiment, the AI-enabled sound identification module 118 utilizes statistical classification algorithms, for example, a Gaussian Mixture Model (GMM)-based clustering algorithm. In various other embodiments, the AI-enabled sound identification module 118 is configured to execute multiple different AI-based algorithms based on what hardware computational resources allow and performance acceptability.

FIG. 7B illustrates an exemplary confusion matrix of sound identification. In the confusion matrix illustrated in FIG. 7B, the rows indicate input sound categories and the columns indicate classified categories.

Figure 8:
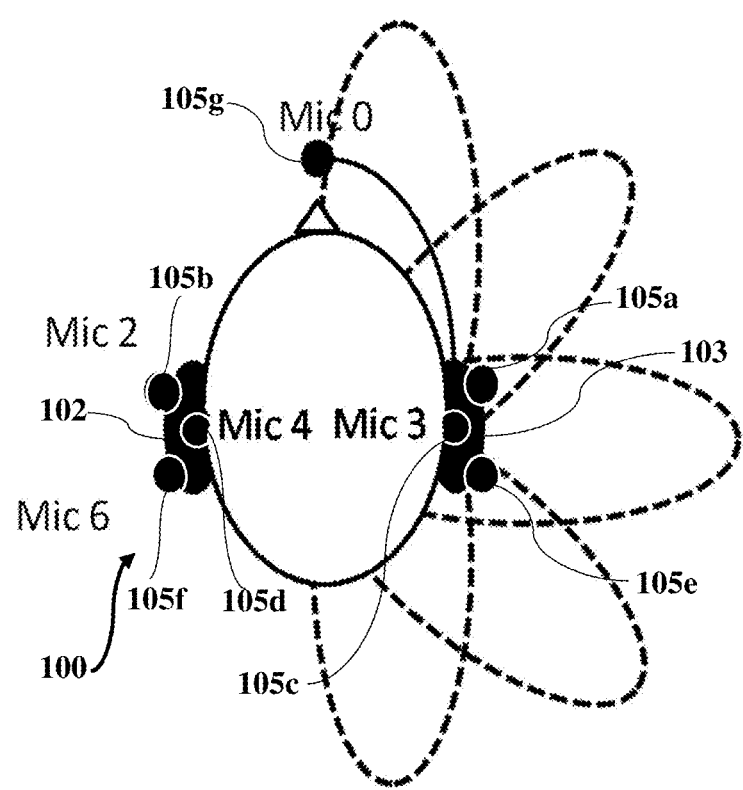
FIG. 8 illustrates a top view of an embodiment of the wearable device, showing generation of multiple acoustic beam patterns pointing to different sound source directions, using two outer microphones disposed on a right hearing member of the wearable device.

FIG. 8 illustrates a top view of an embodiment of the wearable device 100, showing generation of multiple acoustic beam patterns pointing to different sound source directions, using two outer microphones 105a and 105e disposed on a right hearing member, for example, the right ear cup 103, of the wearable device 100. Using two microphones 105a and 105e on the ear cup 103, the beamformer(s) 112 illustrated in FIGS. 3-4, forms multiple acoustic beam patterns simultaneously pointing to different sound source directions as illustrated in FIG. 8, for facilitating provision of three-dimensional (3D) situational awareness. FIG. 8 illustrates the 3D sound full directional awareness solution in the wearable device 100.

Figure 9:
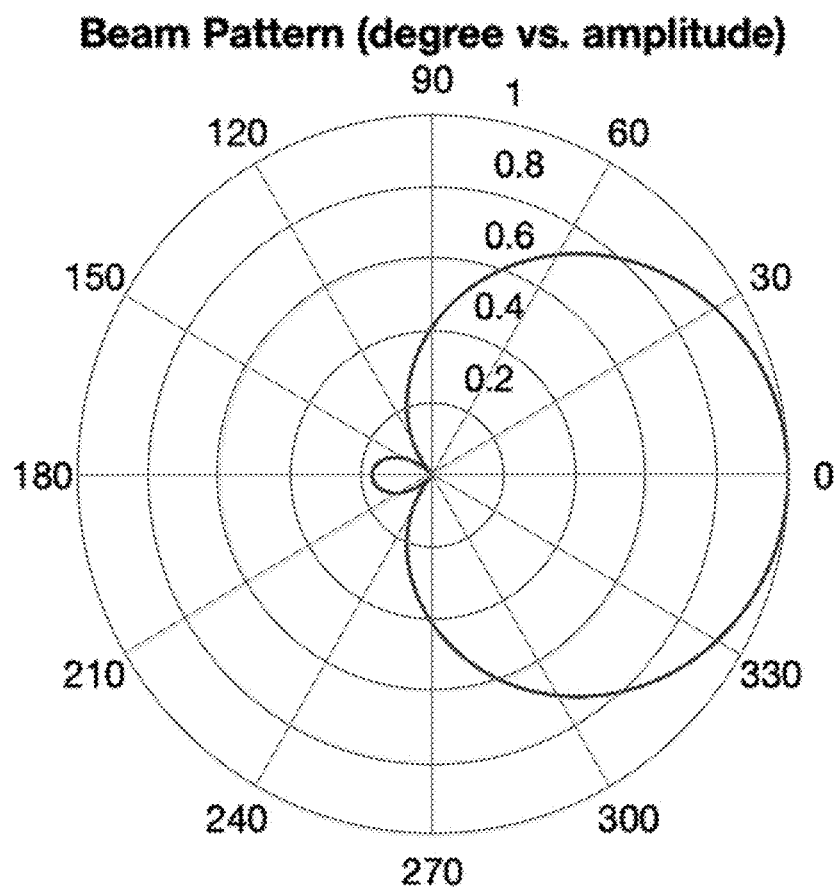
FIG. 9 illustrates a polar plot of an acoustic beam pattern pointing to 0 degrees.

FIG. 9 illustrates a polar plot of an acoustic beam pattern pointing to 0 degrees (front). In an example, compared to an omnidirectional microphone, the microphone array 105 of the wearable device 100 illustrated in FIGS. 1A-1B, provides about 60% attenuation of the sound from 270 degrees (downward) and diminishes the sound from an opposite direction. Hence, the wearable device 100 only amplifies near-field noise or noise off the acoustic beam pattern.

FIG. 10A illustrates a block diagram showing an embodiment of generating three-dimensional (3D) binaural sound using acoustic beamforming, sound source localization, and head-related transfer functions (HRTFs). The system 300 first uses the microphone array 105 to locate one or more sound sources, and then uses the beamformer(s) 112 illustrated in FIG. 3, to form acoustic beam patterns pointing to the corresponding sound source directions. The output sound track of each beamformer 112 that generates the acoustic beam patterns is then converted to binaural sound by the HRTF filters of the corresponding sound source direction. The multi-channel audio signals captured from the microphone array 105 comprising the outer microphones 105b, 105f and 105a, 105e mounted on the ear cups 102 and 103 of the wearable device 100 illustrated in FIG. 8, respectively, are used in the beamformer(s) 112 of the sound source localization unit 111 illustrated in FIG. 3, for beamforming and pre-processing 1001 and for sound source localization 403 concurrently. The beamformer(s) 112 generates multiple acoustic beam patterns where the output signal contains the enhanced sound in the beampattern direction as illustrated in FIG. 8. Using the results from the sound source localization unit 111, the 3D sound generator 117 resynthesizes multiple auditory signals focusing on multiple directions/areas into two channels based on corresponding HRTFs retrieved from the HRTF database 123 as illustrated in FIG. 10A. The 3D sound generator 117 converts the sound captured by the microphone array 105 into a 3D sound using the HRTFs. The resulting two channels are the left and right sound channels configured to playback 3D binaural sound through the speakers 104 and 106, respectively, that rebuilds and also enhances a realistic acoustic scene. As real sound is blocked by the ear cups 102 and 103, the microphone array 105 and the beamformer(s) 112 together reproduce real sound with cues of the sound source directions. The 3D binaural sound generated by the 3D sound generator 117 provides full directional awareness to a user.

Figure 10B:
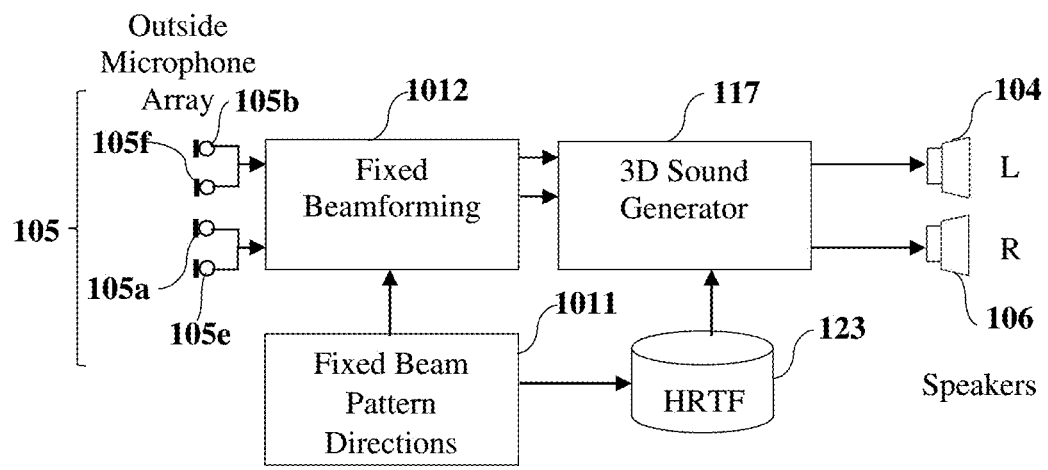
FIG. 10B illustrates a block diagram showing another embodiment of generating three-dimensional binaural sound using fixed beamforming, sound source localization, and head-related transfer functions.

FIG. 10B illustrates a block diagram showing another embodiment of generating three-dimensional (3D) binaural sound using fixed beamforming, sound source localization, and head-related transfer functions (HRTFs). In an embodiment, as a variation of the re-synthesis system disclosed in the description of FIG. 10A, the beamformer(s) 112 illustrated in FIG. 3 performs fixed beamforming 1012 at the microphone array(s) 105 mounted on the ear cups 102 and 103 of the wearable device 100 illustrated in FIG. 8, without using the result of sound source localization. The fixed acoustic beam patterns are predesigned. The microphone array 105 are configured to capture sound from the directions of predesigned acoustic beam patterns. In an embodiment, the beamformer(s) 112 outputs multiple sound tracks, each associated with one acoustic beam pattern, which defines a sound source location. For each output sound track from an acoustic beam pattern, the 3D sound generator 117 applies a pair of HRTF filters associated with the beam pattern direction to output the sound tracks comprising a cue of one sound source direction or location, for left and right ears. The 3D sound generator 117 merges all sound tracks of the HRTF output for the left ear to generate a left sound channel to drive the left speaker 104. Similarly, the 3D sound generator 117 merges all sound tracks of the HRTF output for the right ear to generate a right sound channel to drive the right speaker 106. The 3D sound generator 117 performs the merging operation, for example, using an add operation, a weighted sum operation, or other operations.

In this embodiment, the sound source localization unit 111 illustrated in FIG. 3, that performs sound source localization 403 shown in FIG. 10A is omitted. When the outer microphones 105a, 105e and/or 105b, 105f form multiple fixed acoustic beams steering in different fixed beam pattern directions 1011 of the ambient sound environment, their outputs can be directly adopted to form a full 3D sound field by passing through suitable HRTFs corresponding to the sound field where an acoustic beam is steered. The variation of omitting sound source localization unit 111 in this embodiment overcomes a potential risk that the sound source localization unit 111 may introduce some time delay and may not be perfectly accurate. This variation is able to perceive the entire surrounding sound other than focusing on a particular direction. The 3D sound generator 117 generates 3D binaural sound by applying suitable HRTFs retrieved from the HRTF database 123 to the fixed beamforming output as illustrated in FIG. 10B. The resulting two channels are the left and right sound channels configured to playback the 3D binaural sound through the speakers 104 and 106, respectively, that rebuilds and also enhances a realistic acoustic scene. The 3D binaural sound generated by the 3D sound generator 117 provides full directional awareness to a user.

The generation of 3D sound and in turn the 3D binaural sound in the AI-based system 300 illustrated in FIG. 3, using both non-fixed acoustic beamforming and fixed beamforming, sound source localization, and HRTFs as disclosed in the descriptions of FIGS. 10A-10B, provides full directional and improved auditory awareness with hearing protection to a user. By listening to the output 3D sound, the user can localize the sound source, while their hearing can be sufficiently protected inside the ear cups 102 and 103. When multiple sound sources are detected, the user can hear multiple sounds simultaneously with their directional cues preserved. Moreover, since the sound source directions can be recognized from the 3D sound and voice assistance, the AI-based system 300 further improves the user's situational awareness.

FIG. 11 illustrates a block diagram of an embodiment of an active noise cancelation (ANC) unit 1101 implemented in one of the hearing members, for example, the ear cup 102 of the wearable device 100 shown in FIGS. 1A-1B. The ANC unit 1101 performs functions of one or more of the ANC units 113 and 120 of the system 300 illustrated in FIG. 3 and as disclosed in the descriptions of FIGS. 3-4. The ANC unit 1101 is configured to implement one or more of different ANC methods suitable for headsets. The ANC methods comprise, for example, a feedforward ANC, a feedback ANC, and a hybrid ANC. For implementing feedforward ANC, the ANC unit 1101 utilizes the outer microphones located externally on each ear cup to pick up external ambient noise, and then utilizes the outer microphones to generate an opposite phase signal in the audio path to cancel out the traveled ambient noise inside the ear cup. For implementing feedback ANC, the ANC unit 1101 utilizes the inner microphone located inside each ear cup to pick up ambient noise remaining internally, and then utilizes the inner microphone as a reference to adjust the ANC unit 1101 to generate an opposite phase signal in the audio path to cancel out the traveled ambient noise in the ear cup. For implementing hybrid ANC, the ANC unit 1101 utilizes both the feedforward and feedback paths together, which uses both outer microphones and inner microphones. For hybrid ANC, the ANC unit 1101 generates anti-noise in the same manner as performed in feedforward ANC, and also further adjusts the ANC unit 1101 to refine the anti-noise based on the remaining signal received at the inner microphones, combining the effects of both feedforward ANC and feedback ANC for an optimal ANC result.

In an example, the ANC unit 1101 implementing hybrid ANC in the ear cup 102 of the wearable device 100 is illustrated in FIG. 11. For hybrid ANC, the ANC unit 1101 implements both feedforward ANC and feedback ANC routes. In an embodiment as illustrated in FIG. 11, the ANC unit 1101 comprises a feedforward ANC module 113a and a feedback ANC module 120a to implement a combination of feedforward ANC and feedback ANC, respectively. The feedforward ANC module 113a is operably coupled to the outer microphones 105b and 105f and the speaker 104 as illustrated in FIG. 11. In the feedforward ANC route, the outer microphones 105b and 105f capture the noise, the feedforward ANC module 113a handles the signal processing with low system delay, and the speaker 104 plays anti-noise. The feedforward ANC module 113a utilizes the outer microphones 105b and 105f located externally on the ear cup 102 to pick up external ambient noise, and then utilizes the outer microphones 105b and 105f to generate an opposite phase signal in the audio path to cancel out the traveled ambient noise inside the ear cup 102. In the feedback ANC route, the inner microphone 105d executes feedback adaptation control. In an embodiment, the feedback ANC module 120a is operably coupled to the inner microphone 105d and the speaker 104. The feedback ANC module 120a utilizes the inner microphone 105d located inside the ear cup 102 to pick up ambient noise remaining internally, and then utilizes the inner microphone 105d as a reference to adjust the ANC unit 1101 to generate an opposite phase signal in the audio path to cancel out the traveled ambient noise in the ear cup 102.

In other embodiments, the ANC unit 1101 is configured to implement other methods of active noise cancelation. For example, the ANC unit 1101 is configured to execute an ANC algorithm based on a filtered-x least mean square (FxLMS) or its related mutations. This ANC algorithm utilizes an adaptive filter continuously controlled by a feedback microphone, for example, 105d, located in the ear cup 102, close to the ear, and utilizes the speaker 104 to generate anti-noise, thereby compensating for the true acoustic noise passed through the ear cup 102. In another embodiment, the ANC unit 1101 executes an ANC algorithm comprising two modes, where the first mode comprises off-line acoustic calibration and path(s) learning and calibration, and the second mode comprises real-time active noise control. In the first mode, the speaker 104 plays noise or another sound suitable for calibration and measuring, thereby allowing calibration of the components and learning of the acoustic and electronics path of the system 300. The learned characteristics are used to design the ANC filters. The second mode comprises real-time noise cancelation. In the second mode, by executing the ANC algorithm, the ANC unit 1101 computes and then play the anti-noise from the speaker 104. Meanwhile, the microphone 105d inside the ear cup 102 feeds the residual signal to the ANC unit 1101 for a real-time adaptation to the noise change.

In an embodiment, the ANC unit 1101 is configured to be activated automatically when necessary. The inner microphones 105d and 105c illustrated in FIGS. 1A-1B, measure the noise level in the ear cups 102 and 103, respectively. When the noise level is low, the ANC unit 1101 is in sleep mode for extended battery life. When the noise level is high, that is, when the noise level is above a predetermined threshold, the ANC unit 1101 is triggered to promote extra attenuation for hearing protection. For example, when the noise level is high, the inner microphones 105d and 105c transmit a trigger signal or a wakeup signal to the ANC unit 1101 to wake up the ANC unit 1101 from the sleep mode. As most noise is in the low frequency bands, the energy level in a low frequency band can be used to trigger the ANC unit 1101.

Figure 12:
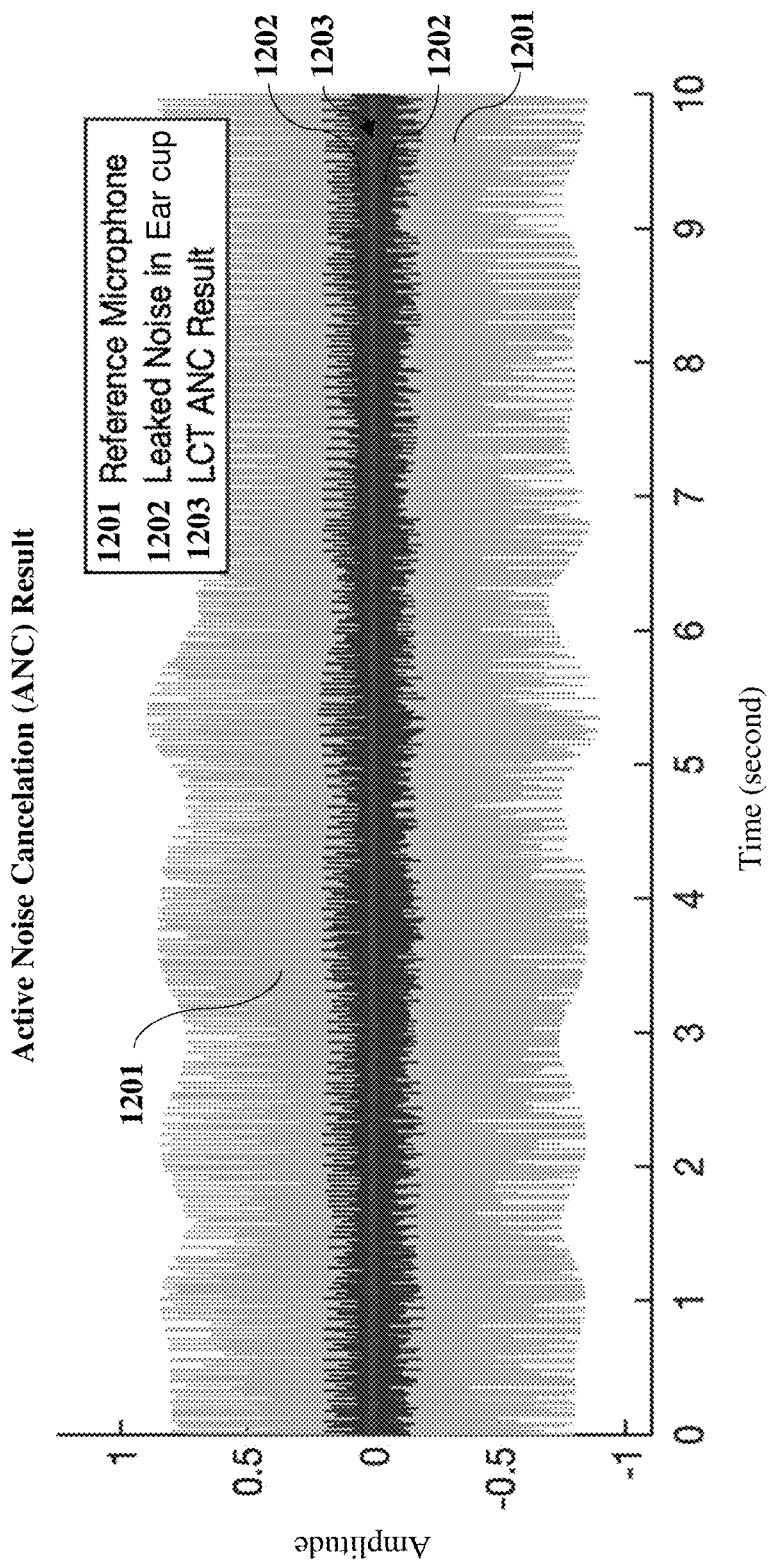
FIG. 12 illustrates a graphical representation showing performance results of active noise cancelation executed by the active noise cancelation unit of the system.

FIG. 12 illustrates a graphical representation showing performance results of active noise cancelation executed by the active noise cancelation (ANC) unit 1101 shown in FIG. 11. As illustrated in FIG. 12, the area referenced by the numeral 1201 indicates the noise received by a reference microphone; the area referenced by the numeral 1202 indicates the leaked noise in the ear cup 102 shown in FIG. 11, and the center line referenced by the numeral 1203 indicates the ANC result of the residual, attenuated sound heard in the ear cup 102. Saturation of the reference microphone causes conventional headsets to work poorly in high noise on flight decks. While conventional tactical headsets provide, for example, about 22 decibels (dB) to about 29 dB of passive hearing protection, the wearable device 100 in the system 300 disclosed herein and illustrated in FIGS. 1A-1B and FIG. 3, is configured with a passive noise reduction rating (NRR) of, for example, about ≥29 dB and more with ear cups, plus about ≥16 dB of active noise attenuation using the ANC technology. Therefore, the total noise attenuation level achieved by the wearable device 100 disclosed herein is, for example, about ≥45 dB.

Figure 13:
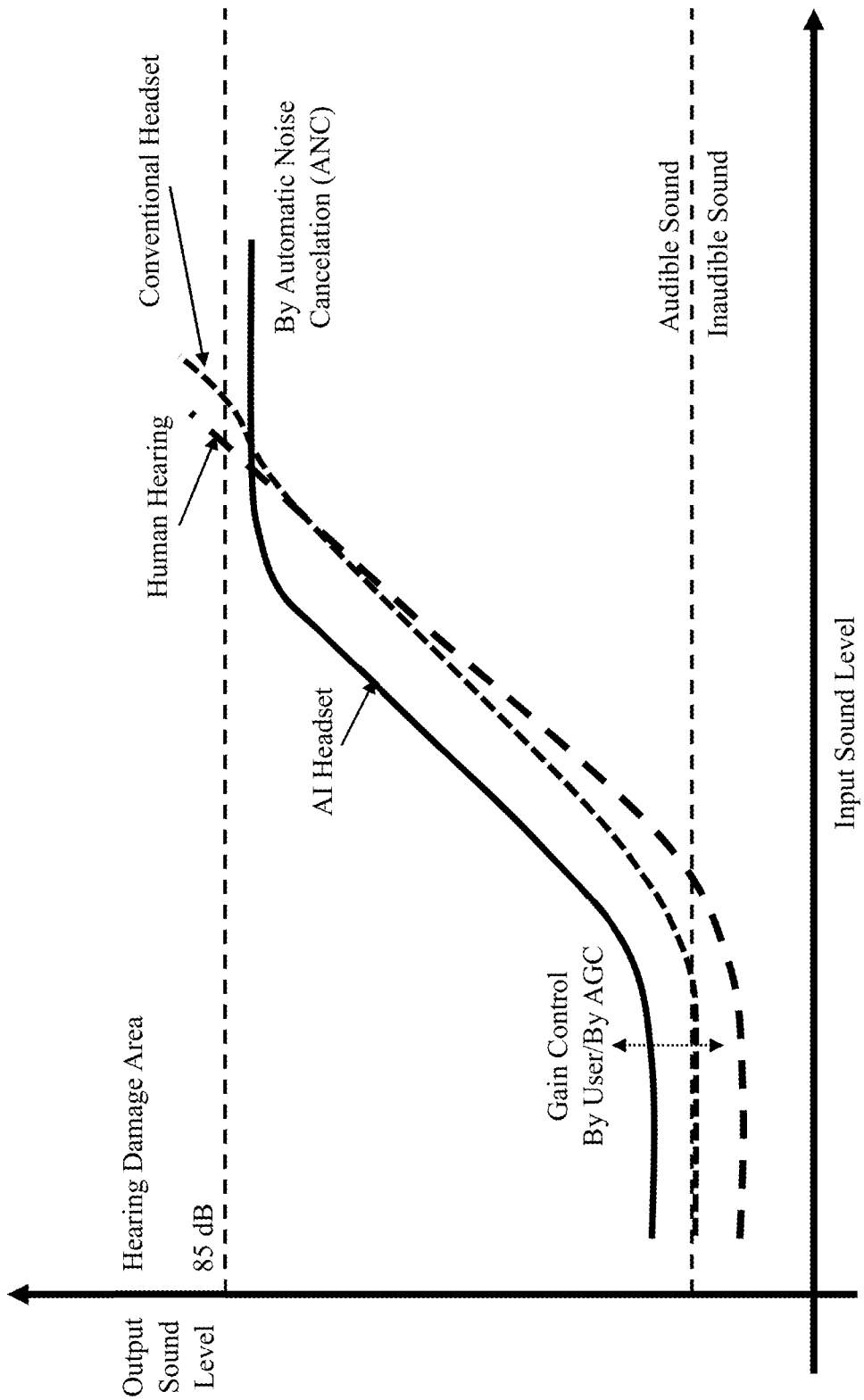
FIG. 13 illustrates a graphical representation showing a comparison of hearing protection and hearing enhancement provided by the wearable device of the system against that of a conventional headset and human hearing.

FIG. 13 illustrates a graphical representation showing a comparison of hearing protection and hearing enhancement provided by the wearable device 100 of the system 300 shown in FIGS. 1A-1B and FIG. 3, against that of a conventional headset and human hearing. The wearable device 100, also referred to as an artificial intelligence (AI) headset, is configured for voice activity detection-based automatic gain control with low noise. A conventional tactical headset typically fails to amplify soft sound or attenuate ambient noise as the conventional tactical headset accepts an uninformative auditory signal such as ambient noise equally as a useful sound event. During testing of the conventional tactical headset in a relatively quiet environment, the conventional tactical headset was found to significantly amplify uninformative ambient noise. Acoustically, uninformative ambient noise is typically generated by thermal agitation of molecules striking a microphone diaphragm or other interference. It was found that the playback noise from the conventional tactical headset is substantially louder than bare ear listening, and almost dominates auditory awareness. For improved auditory awareness and monitoring, in an embodiment, the system 300 executes a function of audio spatial synthesis which uses 3D binaural audio in the system 300. The database 123 of head-related transfer function (HRTF) filters of the system 300 illustrated in FIG. 3, is used to synthesize binaural sound suitable for headphones with spatial hints, thereby allowing the separated sound tracks from the multiple acoustic beam patterns to be processed with the information from sound source localization concurrently, so that a virtual acoustic field with a target location is rebuilt.

Furthermore, to overcome degradation of the signal-to-noise ratio (SNR) and hearing intelligibility caused by conventional tactical headsets that are based on a dynamic range controller (DRC), the system 300 disclosed herein integrates voice activity detection (VAD) and noise reduction functions into the automatic gain control (AGC) unit 121 illustrated in FIG. 3, to provide an intelligent DRC/AGC unit. The VAD algorithm is based on distinguishing an autocorrelation of a signal to an uninformative noise. In an embodiment, the VAD algorithm implements a deep neural network trained by voice and noise data. After training, the DNN is used for real-time voice activity detection. If the sound is determined to be a noise, then the DRC/AGC unit does not amplify the sound. If the sound is an awareness event, then the DRC/AGC unit is configured to attenuate a loud sound and enhance a soft sound as illustrated in FIG. 13, thereby optimally preserving an informative auditory signal and precluding a user's awareness from being disturbed by noise. As illustrated in FIG. 13, by active noise cancelation, the wearable device 100 cancels background noise above a predetermined threshold level, for example, 85 dB, and maintains the output sound level below the predetermined threshold level to preclude hearing damage, thereby providing hearing protection to the user.

Figure 14:
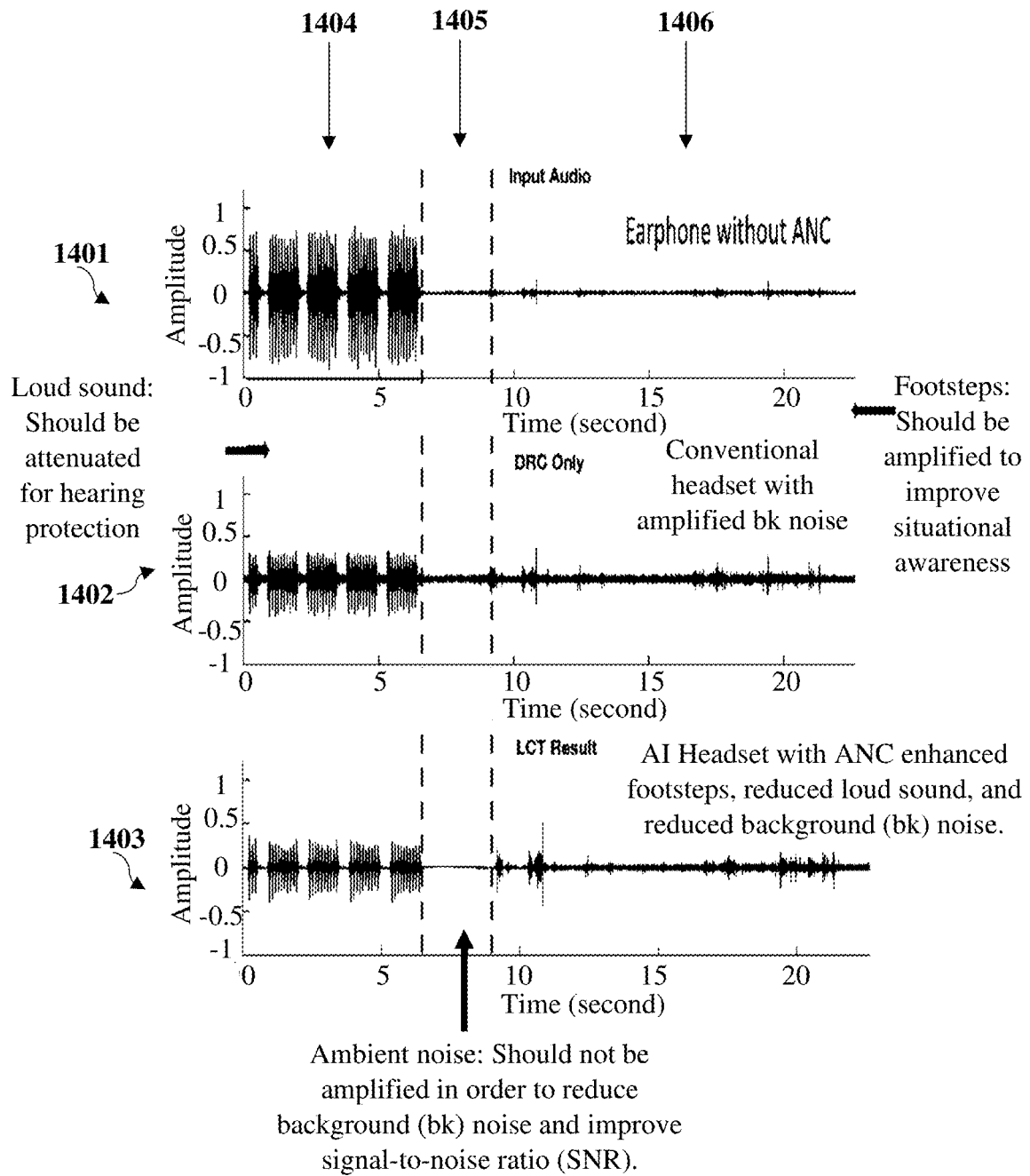
FIG. 14 illustrates a graphical representation showing a comparison of dynamic range control and automatic gain control implemented by the system against that of a conventional dynamic range controller.

FIG. 14 illustrates a graphical representation showing a comparison of dynamic range control (DRC) and automatic gain control (AGC) implemented by the system 300 shown in FIG. 3, against that of a conventional dynamic range controller. The three signal plots 1401, 1402, and 1403 illustrated in FIG. 14, represent an input signal, a conventional DRC, and the intelligent DRC/AGC implemented by the system 300, respectively. The graphical representation indicates three sections referenced by numerals 1404, 1405, and 1406 representing input sound, background noise, and output sound, respectively. On the time domain, when the input sound is a loud sound as indicated in the first section 1404 of the graphical representation, both the methods, that is, the DRC/AGC of the system 300 disclosed herein and the conventional DRC, are found to attenuate the volume of the sound. When the input sound is a background (bk) noise as indicated in the second section 1405 of the graphical representation, the conventional DRC is found to amplify the background noise, since the background noise is also soft, while the DRC/AGC of the system 300 reduces the background noise. When the input sound is a soft sound, for example, soft walking footsteps, as indicated in the third section 1406 of the graphical representation, both the methods, that is, the DRC/AGC of the system 300 disclosed herein and the conventional DRC, are found to amplify the volume of the sound. As illustrated in FIG. 14, only the DRC/AGC implemented by the system 300 is able to reduce the background noise, thereby improving situational awareness.

Figure 15A:
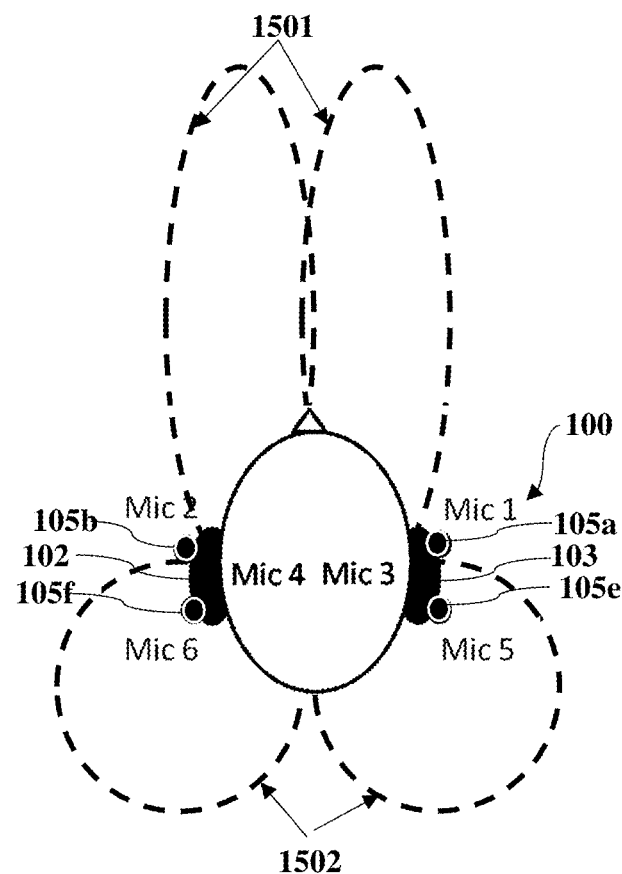
FIGS. 15A-15B illustrate an operation of the system in a voice focused communication mode for face-to-face communication and radio communication, respectively.
Figure 15B:
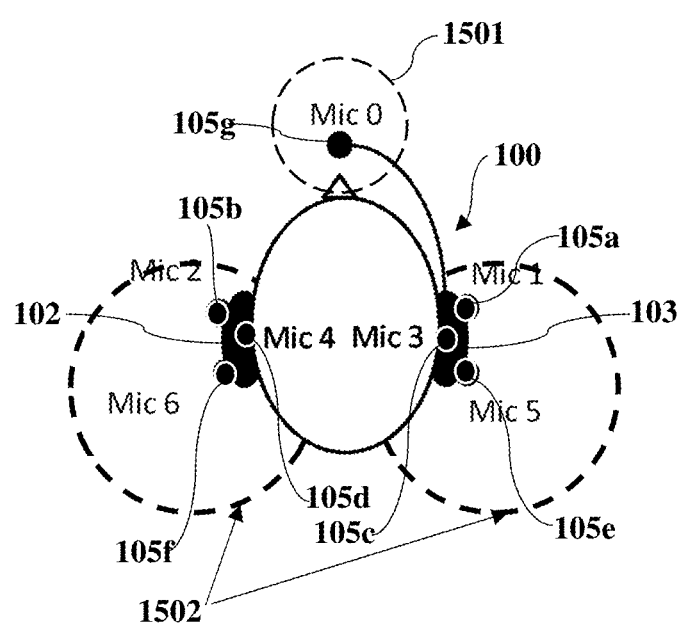

FIGS. 15A-15B illustrate an operation of the system 300 shown in FIG. 3, in a voice focused communication (VFC) mode for face-to-face communication and radio communication, respectively. The system 300 disclosed herein allows for clear two-way communications in noisy environments. Clear two-way communication refers to: (1) removing far end background noise and radio communication channel noise from received signals before sending the signals to a user's ears; and (2) removing the user side background noise and device noise before sending the signals to other users through radio. To ensure clear two-way communications between users, for example, warfighters, in both face-to-face communication and radio communication, and in the presence of high-level noise, in an embodiment, the system 300 disclosed herein operates in the VFC mode, which combines adaptive beamforming, voice activity detection, and noise reduction. In the VFC mode, users of the wearable device 100 can hear clear voice signals with high speech intelligibility to achieve a high level of situational awareness.

In the VFC mode, the active noise cancelation (ANC) unit(s) 113 of the system 300 illustrated in FIG. 3, is constantly running to attenuate ambient noise, for example, greater than 45 dB, at the ear. The beamformer(s) 112 of the system 300 illustrated in FIG. 3, in communication with the microphones 105b, 105f and 105a, 105e on the ear cups 102 and 103, respectively, form acoustic beams 1501 pointing to a front direction as illustrated in FIG. 15A. Moreover, other acoustic beams 1502 are used to obtain sound from other directions except the front direction as illustrated in FIG. 15A. In this embodiment, the acoustic beams 1501 pointing to the front direction receive the face-to-face communication voice, with a portion of ambient noise at the front of the user, and the other acoustic beams 1502 obtain most of the ambient noise surrounding the user. The ANC unit(s) 113 utilizes the ambient noise outside of the front acoustic beam 1501 to cancel the portion of ambient noise included in the front acoustic beam 1501 using an adaptive filter. This active noise cancelation method implemented by the ANC unit(s) 113 is similar to acoustic echo cancelation (AEC) implemented in a voice communication system. AEC is used to prevent sound from a near-end loudspeaker from being transmitted to the far-end so that only speech of a near-end talker is preserved. In the system 300 disclosed herein, adaptive beamforming is performed to prevent the ambient sound in the front acoustic beam 1501 from being transmitted to the user wearing the wearable device 100, and only to preserve the speech at the front. Specifically, this AEC-like process is named generalized sidelobe cancelation (GSC) when used in acoustic beamforming.

When the system 300 operates in the VFC mode, the ANC unit(s) 113 is activated, and the ear cup sound is human speech captured from the front acoustic beam 1501, after noise cancelation/reduction. The VFC mode of the system 300 with the wearable device 100 facilitates face-to-face communication using sound captured from other acoustic beams 1502 to cancel the noise in the front acoustic beams 1501. The VFC mode is also implemented for radio communication, activated by a push-to-talk button from the radio. In contrast to the face-to-face use, in radio communication, the near-end speech is obtained from the boom microphone 105g of the wearable device 100 disposed close to the user's mouth as illustrated in FIG. 15B, and after noise cancelation/reduction, the signal transmits to the radio. The two-way noise reduction operates for radio communication as well. The VFC mode of the system 300 with the wearable device 100 facilitates radio communication using sound captured from other acoustic beams 1502 to cancel the noise in the front acoustic beam 1501 of the boom microphone 105g. The VFC features of the system 300 with the wearable device 100 provides an improvement of, for example, about ≥64 dB in the signal-to-noise ratio for human voice perception, including about ≥45 dB ANC attenuation for better listening.

Figure 16:
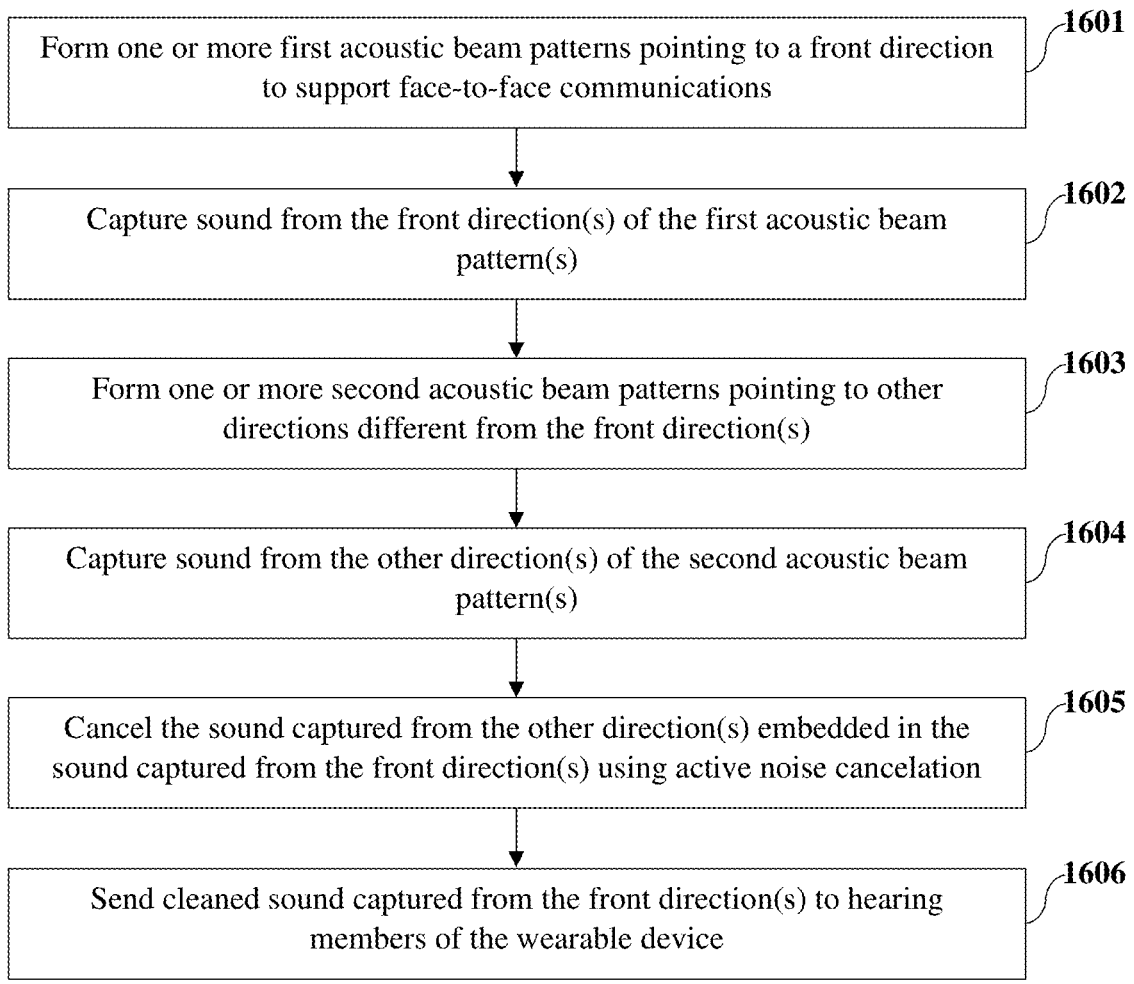
FIG. 16 illustrates a flowchart of an embodiment of a method for implementing clear two-way communications in the voice focused communication mode of the system.

FIG. 16 illustrates a flowchart of an embodiment of a method for implementing clear two-way communications in the voice focused communication (VFC) mode of the system 300 illustrated in FIG. 3. In the VFC mode, the sound source localization unit 111 comprising the microphone array 105 and the beamformer(s) 112 illustrated in FIG. 3, operates as follows. The beamformer(s) 112 forms 1601 one or more first acoustic beam patterns pointing to a front direction to support face-to-face communications. The microphone array 105 captures 1602 sound from the front direction(s) of the first acoustic beam pattern(s). The beamformer(s) 112 forms 1603 one or more second acoustic beam patterns pointing to other directions different from the front direction(s). The microphone array 105 captures 1604 sound from the other direction(s) of the second acoustic beam pattern(s). The active noise cancelation unit(s) 113 of the system 300 illustrated in FIG. 3, cancels 1605 the sound captured from the other direction(s) embedded in the sound captured from the front direction(s) using active noise cancelation. The active noise cancelation unit(s) 113 then sends 1606 cleaned sound captured from the front direction(s) to the hearing members, for example, the ear cups 102 and 103, of the wearable device 100 illustrated in FIGS. 1A-1B. In the cleaned sound, the sound from the other direction(s) has been canceled.

Figure 17:
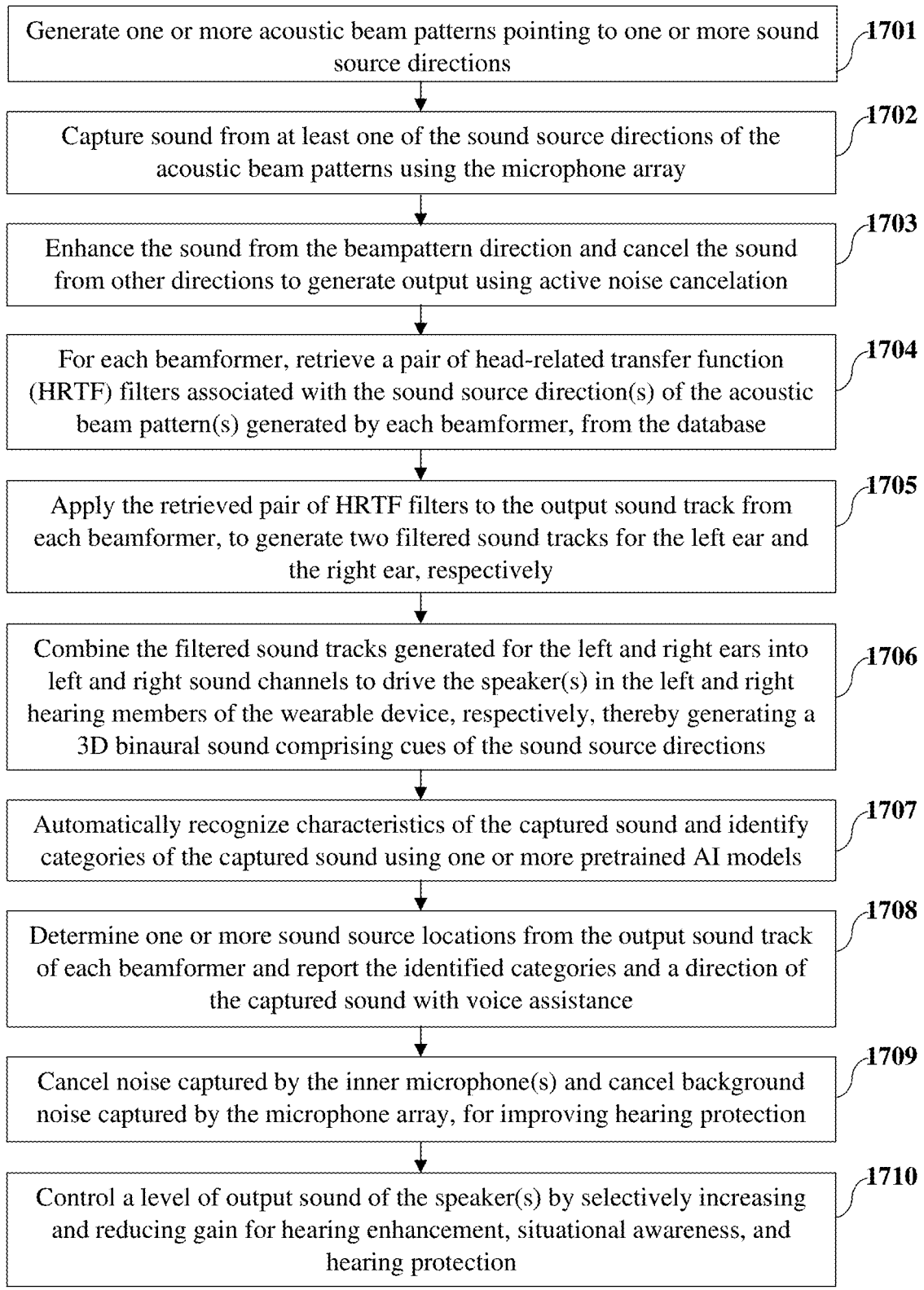
FIG. 17 illustrates a flowchart of an embodiment of a method for providing hearing protection and situational awareness using an AI-based system.

FIG. 17 illustrates a flowchart of an embodiment of a method for providing hearing protection and situational awareness using the artificial intelligence (AI)-based system 300 shown in FIG. 3. The AI-based system 300 comprises a wearable device 100, a pair of speakers 104 and 106, inner microphones 105c and 105d, a sound source localization unit 111 with a microphone array 105 of outer microphones and one or more beamformers 112, and a computation unit 108 as illustrated in FIGS. 1A-1B and FIG. 3. In an embodiment, the computation unit 108 comprises a three-dimensional (3D) sound generator 117, an AI-enabled sound identification module 118, a voice assistant 119, active noise cancelation (ANC) units 113 and 120, an automatic gain control (AGC) unit 121, one or more noise reduction unit(s) 122, and a head-related transfer function (HRTF) database 123 as illustrated in FIG. 3. In the method disclosed herein, the beamformer(s) 112 generates 1701 one or more acoustic beam patterns pointing to one or more sound source directions. The microphone array 105 captures 1702 sound from at least one of the sound source directions of the acoustic beam patterns. The ANC unit 113 enhances 1703 the sound from a particular beampattern direction and cancels the sound from other directions to generate output using active noise cancelation.

For each beamformer 112, the 3D sound generator 117 retrieves 1704 a pair of HRTF filters associated with the particular sound source direction(s) of the acoustic beam pattern(s) generated by each beamformer 112, from the database 123. The 3D sound generator 117 applies 1705 the retrieved pair of HRTF filters to the output sound track from each beamformer 112, to generate two filtered sound tracks for the left ear and the right ear, respectively. Each of the two filtered sound tracks represents the sound captured from the particular sound source direction(s) of the acoustic beam pattern(s) and comprises a cue of the particular sound source direction(s). The 3D sound generator 117 combines 1706 the filtered sound tracks generated for the left ear into a left sound channel to drive the speaker(s) 104 in the left ear cup 102 of the wearable device 100, and combines the filtered sound tracks generated for the right ear into a right sound channel to drive the speaker(s) 106 in the right ear cup 103 of the wearable device 100, thereby generating a 3D binaural sound comprising cues of the sound source directions. The speakers 104 and 106 in the ear cups 102 and 103 of the wearable device 100, respectively, reproduce real sound outside of the wearable device 100.

In an embodiment, the AI-enabled sound identification module 118 automatically recognizes 1707 characteristics of the captured sound and identifies categories of the captured sound using one or more pretrained AI models. In an embodiment, the voice assistant 119, operably coupled to the pair of speakers 104 and 106, and in communication with the AI-enabled sound identification module 118 and the sound source localization unit 111, determines 1708 one or more sound source locations from the output sound track of each beamformer 112 and reports the identified categories of the captured sound and a direction of the captured sound with voice assistance via the pair of speakers 104 and 106 and/or other interface devices. In an embodiment, the ANC unit 120 cancels 1709 noise captured by the inner microphone(s) 105c and 105d and cancels background noise captured by the microphone array 105, for improving hearing protection. In another embodiment, the AGC unit 121 controls 1710 a level of output sound of the speakers 104 and 106 by selectively increasing gain when a level of the output sound is substantially low for hearing enhancement and situational awareness, and reducing the gain when a level of the output sound is substantially high for hearing protection. Although FIG. 16 illustrates a particular sequence of method steps performed by the system 300, the scope of the method disclosed herein is not limited to the particular sequence of method steps illustrated in FIG. 16, but extends to include any other sequence of the method steps or combination of the method steps disclosed herein. Computer program instructions, stored on a non-transitory, computer-readable storage medium and executable by the processor(s) 110 illustrated in FIG. 3, implement the processes of various embodiments disclosed above and perform additional steps that may be required and contemplated for providing hearing protection and situational awareness. When the computer program instructions are executed by the processor(s) 110, the computer program instructions cause the processor(s) 110 to perform the steps of the method for providing hearing protection and situational awareness as disclosed in the descriptions of FIGS. 1A-16. In an embodiment, a single piece of computer program code comprising computer program instructions performs one or more steps of the method disclosed in the descriptions of FIGS. 1A-16.

The system 300 with the wearable device 100 disclosed herein implements a 3D full directional awareness functionality that is far beyond the conventional ambient listening feature of headsets. The system 300 provides voice assistance with full directional awareness. Based on advanced feature extraction and deep neural network (DNN) methods, the sound identification algorithm executed by the AI-enabled sound identification module 118 is capable of recognizing an object such as a tank, a gunshot, a helicopter, etc., from its sound. The AI-enabled sound identification module 118 operates concurrently with the sound source localization unit 111, to identify a direction of the sound. The system 300 uses an increased number of microphones 105a, 105e, and 105b, 105f in an array 105 on the wearable device 100 to identify sound source directions. Using the sound source direction information, the voice assistant 119 provides intelligent voice assistance verbally indicating the identified direction and the object to a user. Moreover, the voice assistance is also rendered with binaural effects coming from the identified direction. This binaural notification alerts the user in a more intuitive way, so that the user is able to respond faster. Moreover, the system 300 with the wearable device 100 optimizes auditory detection and localization in helmet and in-ear communications in high- and low-noise environments. Furthermore, the system 300 with the wearable device 100 demonstrates improved and clear communications in actual scenarios, for example, in ground/maritime operations, and implements noise monitoring without adverse effects on operational performance.

The system 300 with the wearable device 100 disclosed herein reduces high background noise, for example, a constant "hiss" noise, produced by conventional headsets. The system 300 provides awareness cues of sound source directions or locations; generates 3D binaural sound comprising the cues of the sound source directions or locations as opposed to only stereo sound generated by conventional headsets; measures energy at low frequency bands; performs active noise cancelation; and selectively amplifies informative, desired sounds as opposed to conventional headsets that amplify or attenuate all sounds. The system 300 performs an intelligent selection of desired and undesired sound. The ambient listening function of the system 300 is dependent on the microphone array 105 comprising multiple microphones, for example, 105a, 105e, and 105b, 105f, with directionality and noise reduction. The system 300 amplifies far-field soft sound in a silent environment to enhance awareness. Unlike conventional headsets that amplify unwanted sounds such as soft sounds, for example, breathing, footsteps, rubbing cloth, etc., generated when a user is close to an air conditioner or when the user is moving, and allow these unwanted sounds to dominate an acoustic scene, the system 300 intelligently amplifies desired sounds and attenuates or cancels undesired sounds, thereby enhancing situational awareness, hearing sensitivity, and intelligibility.

Furthermore, unlike conventional headsets that remove all directional information from the sound which requires the user to pay much more attention using visual observation to distinguish the sound source and its location, distance, and direction, the system 300 generates 3D binaural sound comprising cues of the sound source directions or locations for enabling the wearable device 100 to reproduce the outside sound field, thereby improving situational awareness. The system 300 has substantially higher performance than conventional headsets due acoustic beamforming, noise reduction, and 3D sound technologies implemented therein. Considering the user interface, the system 300 disclosed herein provides voice assistance to report an identified sound and its direction. In hearing protection, the system 300 performs active noise cancelation for active hearing protection; comprises ear cups 102 and 103 for passive hearing protection; and performs noise monitoring and dosimetry. In communication, the system 300 performs two-way noise reduction to improve speech intelligibility and to support both radio and face-to-face communications. In hardware and battery life, the system 300 utilizes an advanced ultra-low power consumption chip set, which operates for up to, for example, about 622 hours, on two AA batteries.

The advancement of the system 300 with the wearable device 100, herein referred to as the "AI headset", is measured in the following specifications:
  (a) Noise attenuation: For hearing protection, the AI headset provides, for example, ≥35 dB of noise attenuation to impulse sounds such as gunshots, and ≥45 dB of noise attenuation to continuous sounds such as a helicopter sound.
  (b) Low level sound enhancement: For situational awareness, the AI headset provides, for example, ≥12 dB gain for a sound level below 30 dB.
  (c) Speech intelligibility: The speech intelligibility performance of the AI headset on human subjects is the same as or better than conventional headsets used in the field. The AI headset passes, for example, the Modified Rhyme Test (MRT) or similar test.
  (d) Sound identification (ID) accuracy: The accuracy of sound identification in the AI headset is, for example, greater than 85%.
  (e) Sound location tolerance range: The error of sound source localization in the AI headset is, for example, less than 15 degrees.
  (f) Response time: The sound identification and sound source localization response time in the AI headset is, for example, less than 1 second.
  (g) Easy and comfortable to wear and use: The AI headset is configured to be easy to use and comfortable to wear. The weight of the AI headset is similar to conventional headsets. The AI headset is manufactured in a size configured to fit all users.

In addition to conventional features such as hearing protection, soft sound amplification, and radio communications, the AI headset is configured to automatically detect the sound direction and sound ID and inform users by voice assistance. For example, through the AI headset, the user can hear a voice: " . . . [footsteps sound] 4 o'clock footsteps . . . " or " . . . [gunshot sound] 8 o'clock gunshot . . . ". The microphone array 105/sound source localization unit 111 in the AI headset detects the sound direction and the computation unit 108 of the AI headset generates a 3D binaural sound, which allows users to feel the 3D acoustic scene and understand that the sound is from the detected sound direction, thereby substantially improving situational awareness and users' safety and reducing user training time. Furthermore, the AI headset is configured to cancel unwanted noisy sounds such as a helicopter sound, for hearing protection and for improving speech intelligibility in radio communications. Due to noise reduction and active noise cancelation technology, the noise level of the AI headset is substantially reduced to improve speech intelligibility, communication clarity, and situational awareness. The system 300 disclosed herein has applications in communications, gaming, training, etc.

It is apparent in different embodiments that the various methods, algorithms, and computer-readable programs disclosed herein are implemented on non-transitory, computer-readable storage media appropriately programmed for computing devices. The non-transitory, computer-readable storage media participate in providing data, for example, instructions that are read by a computer, a processor, or a similar device. In different embodiments, the "non-transitory, computer-readable storage media" also refer to a single medium or multiple media, for example, a centralized database, a distributed database, and/or associated caches and servers that store one or more sets of instructions that are read by a computer, a processor, or a similar device. The "non-transitory, computer-readable storage media" also refer to any medium capable of storing or encoding a set of instructions for execution by a computer, a processor, or a similar device and that causes a computer, a processor, or a similar device to perform any one or more of the steps of the method disclosed herein. In an embodiment, the computer programs that implement the methods and algorithms disclosed herein are stored and transmitted using a variety of media, for example, the computer-readable media in various manners. In an embodiment, hard-wired circuitry or custom hardware is used in place of, or in combination with, software instructions for implementing the processes of various embodiments. Therefore, the embodiments are not limited to any specific combination of hardware and software. Various aspects of the embodiments disclosed herein are implemented as programmed elements, or non-programmed elements, or any suitable combination thereof.

Where databases are described such as the head-related transfer function (HRTF) database 123 illustrated in FIG. 3, it will be understood by one of ordinary skill in the art that (i) alternative database structures to those described may be employed, and (ii) other memory structures besides databases may be employed. Any illustrations or descriptions of any sample databases disclosed herein are illustrative arrangements for stored representations of information. In another embodiment, despite any depiction of the databases as tables, other formats including relational databases, object-based models, and/or distributed databases are used to store and manipulate the data types disclosed herein. In an embodiment, object methods of a database are used to implement various processes such as those disclosed herein. In another embodiment, the databases are, in a known manner, stored locally or remotely from a device that accesses data in such a database. In embodiments where there are multiple databases, the databases are integrated to communicate with each other for enabling simultaneous updates of data linked across the databases, when there are any updates to the data in one of the databases.

The foregoing examples and illustrative implementations of various embodiments have been provided merely for explanation and are in no way to be construed as limiting the embodiments disclosed herein. While the embodiments have been described with reference to various illustrative implementations, drawings, and techniques, it is understood that the words, which have been used herein, are words of description and illustration, rather than words of limitation. Furthermore, although the embodiments have been described herein with reference to particular means, materials, techniques, and implementations, the embodiments herein are not intended to be limited to the particulars disclosed herein; rather, the embodiments extend to all functionally equivalent structures, methods and uses, such as are within the scope of the appended claims. It will be understood by those skilled in the art, having the benefit of the teachings of this specification, that the embodiments disclosed herein are capable of modifications and other embodiments may be effected and changes may be made thereto, without departing from the scope and spirit of the embodiments disclosed herein.

We claim:

1. A system for providing hearing protection and situational awareness, the system comprising:
    a wearable device comprising hearing members, wherein the hearing members comprise a left hearing member configured to be disposed on a left ear of a user, and a right hearing member configured to be disposed on a right ear of the user;
    one or more speakers disposed at an inner location of each of the hearing members of the wearable device;
    a sound source localization unit operably coupled to the left hearing member and the right hearing member of the wearable device, the sound source localization unit comprising:
        a plurality of beamformers, each configured to generate one acoustic beam pattern pointing to one direction;
        an array of four or more outer microphones comprising two or more microphones disposed at outer locations of each of the left hearing member and the right hearing member of the wearable device, wherein the array of four or more outer microphones is configured to capture sound from the plurality of acoustic beam patterns, pointing to outside of the hearing members, and wherein each of the plurality of beamformers is configured to output a sound track, each sound track associated with the captured sound in the direction of the corresponding acoustic beam pattern;
        a pair of inner microphones comprising one inner microphone disposed at an inner location of each of the left hearing member and the right hearing member of the wearable device, wherein the pair of inner microphones is configured to facilitate active noise cancelation;
    a computation unit disposed in one or more of the hearing members of the wearable device and operably coupled to the array of four or more outer microphones and the pair of inner microphones disposed at an inner location of each of the hearing members of the wearable device, the computation unit comprising:
        at least one processor;
        a memory unit operably and communicatively coupled to the at least one processor, wherein the memory unit is configured to store a database of head-related transfer function filters, and computer program instructions defined by a plurality of signal processing modules and executable by the at least one processor;
        the signal processing modules comprising at least one sound generator configured to:
            for each of the plurality of beamformers, retrieve a pair of head-related transfer function filters associated with the direction of the plurality of acoustic beam patterns generated by each of the plurality of beamformers, from the database;
            apply the retrieved corresponding pair of head-related transfer function filters to the output sound track from each of the plurality of beamformers, to generate a pair of filtered sound tracks, one for the left ear and another one for the right ear, wherein each of the filtered sound tracks represents the sound captured from the direction of the corresponding acoustic beam pattern;
            combine the filtered sound tracks generated for the left ear into a left sound channel to drive at least one of the one or more speakers in the left hearing member of the wearable device, and combine the filtered sound tracks generated for the right ear into a right sound channel to drive at least one of the one or more speakers in the right hearing member of the wearable device, thereby generating a binaural sound comprising cues of the sound source directions, wherein the one or more speakers in the each of the hearing members of the wearable device reproduce real sound outside of the wearable device, whereby output sounds from the wearable device comprise a cue of at least one of one or more sound source directions;
        the signal processing modules further comprising an artificial intelligence-enabled sound identification module configured to automatically recognize characteristics of the captured sound and identify categories of the captured sound using one or more pretrained artificial intelligence models;
        the signal processing modules further comprising a voice assistant operably coupled to the one or more speakers and, in communication with the artificial intelligence-enabled sound identification module and the sound source localization unit, configured to determine one or more sound source locations from the output sound track of each of the plurality of beamformers and to report the identified categories of the captured sound and a direction of the captured sound with voice assistance via one of the one or more speakers and one or more other interface devices; and
        the signal processing modules further comprising a set of active noise cancellation units and a set of noise reduction units for utilizing information in both a spatial domain and a temporal domain to cancel and/or reduce noise, thereby ensuring hearing protection and improving signal-to-noise ratio.

2. The system of claim 1, wherein the pair of inner microphones is configured as a noise dosimeter to monitor and record sound levels within the hearing members of the wearable device, and to communicate the recorded sound levels to a storage unit for noise level analysis and review activities.

3. The system of claim 1, wherein the signal processing modules further comprise an automatic gain control unit configured to control a level of output sound of the one or more speakers by selectively increasing gain when a level of the output sound is substantially low for hearing enhancement and situational awareness, and reducing the gain when the level of the output sound is substantially high for hearing protection.

4. The system of claim 1, further comprising a supplementary microphone operably coupled to an adjustable arm extending from one of the hearing members of the wearable device, wherein the supplementary microphone is configured to allow the user to speak thereinto for facilitating two-way communications.

5. The system of claim 1, wherein the wearable device is a headset, and wherein the hearing members are ear cups.

6. The system of claim 1, wherein the set of active noise cancellation units use sound from each of other of the plurality of beamformers to cancel the noise in each of the plurality of beamformers, thereby using spatial information to perform noise cancelation, and thereby improving the signal-to-noise (SNR) of the output of the beamformers.

7. The system of claim 1, wherein, for each sound track, the set of active noise cancellation units apply models or filters to reduce background noise, thereby using temporal information for noise reduction.

8. The system of claim 1, wherein the set of active noise cancellation units execute active noise cancelation to cancel background noise that leaks into the hearing members.

9. A system for providing hearing protection and situational awareness, the system comprising:
  a wearable device comprising hearing members, wherein the hearing members comprise a left hearing member configured to be disposed on a left ear of a user, and a right hearing member configured to be disposed on a right ear of the user;
  one or more speakers disposed at an inner location of each of the hearing members of the wearable device;
  a sound source localization unit operably coupled to the left hearing member and the right hearing member of the wearable device, the sound source localization unit comprising:
    a plurality of beamformers, each configured to generate one acoustic beam pattern pointing to one direction;
    an array of four or more outer microphones comprising two or more microphones disposed at outer locations of each of the left hearing member and the right hearing member of the wearable device, wherein the array of four or more outer microphones is configured to capture sound from the plurality of acoustic beam patterns, pointing to outside of the hearing members, and wherein each of the plurality of beamformers is configured to output a sound track, each sound track associated with the captured sound in the direction of the corresponding acoustic beam pattern;
  a pair of inner microphones comprising one inner microphone disposed at an inner location of each of the left hearing member and the right hearing member of the wearable device, wherein the pair of inner microphones is configured to facilitate active noise cancelation;
  a computation unit disposed in one or more of the hearing members of the wearable device and operably coupled to the array of four or more outer microphones and the pair of inner microphones disposed at an inner location of each of the hearing members of the wearable device, the computation unit comprising:
    at least one processor;
    a memory unit operably and communicatively coupled to the at least one processor, wherein the memory unit is configured to store a database of head-related transfer function filters, and computer program instructions defined by a plurality of signal processing modules and executable by the at least one processor; and
    the signal processing modules comprising:
      at least one sound generator configured to:
        for each of the plurality of beamformers, retrieve a pair of head-related transfer function filters associated with the direction of the plurality of acoustic beam patterns generated by each of the plurality of beamformers, from the database;
        apply the retrieved corresponding pair of head-related transfer function filters to the output sound track from each of the plurality of beamformers, to generate a pair of filtered sound tracks, one for the left ear and another one for the right ear, wherein each of the filtered sound tracks represents the sound captured from the direction of the corresponding acoustic beam pattern;
        combine the filtered sound tracks generated for the left ear into a left sound channel to drive at least one of the one or more speakers in the left hearing member of the wearable device, and combine the filtered sound tracks generated for the right ear into a right sound channel to drive at least one of the one or more speakers in the right hearing member of the wearable device, thereby generating a binaural sound comprising cues of the sound source directions, wherein the one or more speakers in the each of the hearing members of the wearable device reproduce real sound outside of the wearable device, whereby output sounds from the wearable device comprise a cue of at least one of one or more sound source directions;
      the signal processing modules further comprising an artificial intelligence-enabled sound identification module configured to automatically recognize characteristics of the captured sound and identify categories of the captured sound using one or more pretrained artificial intelligence models;
      the signal processing modules further comprising a voice assistant operably coupled to the one or more speakers and, in communication with the artificial intelligence-enabled sound identification module and the sound source localization unit, configured to determine one or more sound source locations from the output sound track of each of the plurality of beamformers and to report the identified categories of the captured sound and a direction of the captured sound with voice assistance via one of the one or more speakers and one or more other interface devices;
      the signal processing modules further comprising a set of active noise cancellation units and a set of noise reduction units for utilizing information in both a spatial domain and a temporal domain to cancel and/or reduce noise, thereby ensuring hearing protection and improving signal-to-noise ratio; and
      the signal processing modules further comprising an automatic gain control unit configured to control a level of output sound of the one or more speakers by selectively increasing gain when a level of the output sound is substantially low for hearing enhancement and situational awareness, and reducing the gain when the level of the output sound is substantially high for hearing protection.

10. The system of claim 9, wherein the pair of inner microphones is configured as a noise dosimeter to monitor and record sound levels within the hearing members of the wearable device, and to communicate the recorded sound levels to a storage unit for noise level analysis and review activities.

11. The system of claim 9, further comprising a supplementary microphone operably coupled to an adjustable arm extending from one of the hearing members of the wearable device, wherein the supplementary microphone is configured to allow the user to speak thereinto for facilitating two-way communications.

12. The system of claim 9, wherein the wearable device is a headset, and wherein the hearing members are ear cups.

13. The system of claim 9, wherein the set of active noise cancellation units use sound from each of other of the plurality of beamformers to cancel the noise in each of the plurality of beamformers, thereby using spatial information to perform noise cancelation, and thereby improving the signal-to-noise (SNR) of the output of the beamformers.

14. The system of claim 9, wherein, for each sound track, the set of active noise cancellation units apply models or filters to reduce background noise, thereby using temporal information for noise reduction.

15. The system of claim 9, wherein the set of active noise cancellation units execute active noise cancelation to cancel background noise that leaks into the hearing members.

* * * * *